United States Patent
Cameron et al.

(10) Patent No.: US 6,426,359 B1
(45) Date of Patent: Jul. 30, 2002

(54) PREVENTION AND TREATMENT OF SKELETAL DISORDER WITH EP2 RECEPTOR SUBTYPE SELECTIVE PROSTAGLANDIN E2 AGONISTS

(75) Inventors: Kimberly O. Cameron, East Lyme; Hua Z. Ke, Ledyard; Bruce A. Lefker, Gales Ferry; Robert L Rosati, Mystic; David D. Thompson, Gales Ferry, all of CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/331,078

(22) PCT Filed: Nov. 27, 1997

(86) PCT No.: PCT/IB97/01483

§ 371 (c)(1), (2), (4) Date: Jun. 11, 1999

(87) PCT Pub. No.: WO98/27976

PCT Pub. Date: Jul. 2, 1998

Related U.S. Application Data

(60) Provisional application No. 60/033,569, filed on Dec. 20, 1996, now abandoned.

(51) Int. Cl.⁷ ...................... A61K 31/41; C07C 317/00; C07D 257/04
(52) U.S. Cl. ...................... 514/381; 514/488; 514/601; 435/366; 548/252; 548/254; 549/71; 568/30
(58) Field of Search ................................. 514/381, 488; 514/601; 548/252, 254; 549/71; 568/30; 435/366

(56) References Cited

U.S. PATENT DOCUMENTS

| | | |
|---|---|---|
| 4,018,892 A | 4/1977 | Walsh |
| 4,033,996 A | 7/1977 | Cragoe, Jr. et al. |
| 4,112,236 A | 9/1978 | Bicking et al. |
| 5,409,911 A | 4/1995 | Tyler et al. |
| 5,605,814 A | 2/1997 | Abramovitz et al. |
| 5,698,598 A | 12/1997 | Woodward et al. |
| 5,759,789 A | 6/1998 | Abramovitz et al. |
| 6,288,120 B1 | 9/2001 | Cameron et al. ........... 514/605 |

FOREIGN PATENT DOCUMENTS

| | | | |
|---|---|---|---|
| EP | 0338796 | 3/1993 | |
| EP | 0860430 | 8/1998 | |
| HU | 199411 | 5/1988 | ......... C07C/405/00 |
| WO | WO9506664 | 3/1995 | |
| WO | WO9827976 | 7/1998 | |

OTHER PUBLICATIONS

K. Nemoto, et al., Prostaglandins 54:713–725, 1997, pp. 713–725, "Molecular Cloning and Expression of a Rat Prostaglandin $E_2$ Receptor of the $EP_2$ Subtype".

M. Suda, et al., Endocrinology vol. 137, No. 5, pp. 1698–1705, "Prostaglandin E Receptor Subtypes in Mouse Osteoblastic Cell Line (1996)".

S. Kasugai, et al., Bone, vol. 17, No. 1, Jul. 1995, pp. 1–4, "Expression of Prostaglandin E Receptor Subtypes in Bone: Expression of $EP_2$ in Bone Development".

A. Scutt, et al., Prostaglandins 49:383–395, 1995 "$PGE_2$ Induces the Transition from Non–Adherent to Adherent Bone Marrow Mesenchymal Precursor Cells Via a cAMP/$EP_2$–Mediated Mechanism".

F. N. Woodiel, et al., Journal of Bone and Mineral Research, vol. 11, No. 9, 1996 pp. 1249–1255, "Anabolic Effects of Prostaglandins in Cultured Fetal Rate Calvariare: Structure–Activity Relations and Signal Transduction Pathway".

C. D. Funk, et al., The Journal of Biological Chemistry, 1993 vol. 268, No. 35 pp. 26767–26772, "Cloning and Expression of a cDNA for the Human Prostaglandin E Receptor $EP_1$ Subtype".

J. W. Regan, et al., The American Society for Pharmacology and Experimental Therapeutics,—Molecular Pharmacology, 46:213–220, 1994 "Cloning of a Novel Human Prostaglandin Receptor with Characteristics of the Pharmacologically Defined $EP_2$ Subtype".

J. Yang., et al., Biochemical and Biophysical Research Communications, vol. 198, No. 3, 1994, pp. 999–1006, "Cloning and Expression of the EP3–Subtype of Human Receptors for Prostaglandin E2".

L. Bastien, The Journal of Biological Chemistry, vol. 269, No. 16, Apr. 22, pp. 11873–11877, 1994, "Cloning, Functional Expression, and Characterization of the Human Prostaglandin $E_2$ Receptor $EP_2$ Subtype".

T. Ohta, et al., The Journal of Pharm & Experimental Thereapeutics, vol. 275, No. 1, 1995, pp. 450–455, "TEI–3313, a Novel Prostaglandin $A_1$ Derivative, Prevents Bone Loss and Enhances Bone Formation in Immobilized Male Rats".

J. Bone Miner. Res. 1996, 11(supp.):S174, (S337,S338).

*Primary Examiner*—T. A. Solola
(74) *Attorney, Agent, or Firm*—Peter C. Richardson; Gregg C. Benson; Martha G. Munchhof

(57) ABSTRACT

This invention relates to the use of EP2 receptor subtype selective prostaglandin E2 agonists to augment bone mass including the prevention and treatment of skeletal disorders in mammals, including humans.

19 Claims, No Drawings

PREVENTION AND TREATMENT OF SKELETAL DISORDER WITH EP2 RECEPTOR SUBTYPE SELECTIVE PROSTAGLANDIN E2 AGONISTS

This application was filed under 35 U.S.C. §371 based on PCT/IB97/01483 which was filed Nov. 27, 1997 and which claims priority from U.S. provisional application serial No. 60/033,569 which was filed on Dec. 20, 1996 and is now abandoned.

BACKGROUND OF INVENTION

This invention relates to the use of EP2 receptor subtype selective prostaglandin E2 agonists to augment bone mass including the prevention and treatment of skeletal disorders in mammals, including humans.

Osteoporosis is a systemic skeletal disorder, characterized by low bone mass and deterioration of bone tissue, with a consequent increase in bone fragility and susceptibility to fracture. In the U.S., the condition affects more than 25 million people and causes more than 1.3 million fractures each year, including 500,000 spine, 250,000 hip and 240,000 wrist fractures annually. Hip fractures are the most serious, with 5–20% of patients dying within one year, and over 50% of survivors being incapacitated.

The elderly are at greatest risk of osteoporosis, and the problem is therefore predicted to increase significantly with the aging of the population. Worldwide fracture incidence is forecast to increase three-fold over the next 60 years, and one study estimates that there will be 4.5 million hip fractures worldwide in 2050.

Women are at greater risk of osteoporosis than men. Women experience a sharp acceleration of bone loss during the five years following menopause. Other factors that increase the risk include smoking, alcohol abuse, a sedentary lifestyle and low calcium intake.

In addition to hip fractures numbering approximately 250,000/year in the U.S., approximately, 20–25 million women and an increasing number of men have detectable vertebral fractures. Hip fracture is associated with a 12% mortality rate within the first two years and with a 30% rate of patients requiring nursing home care after the fracture. While this is already significant, the economic and medical consequences of convalescence due to slow or imperfect healing of these bone fractures is expected to increase, due to the aging of the general population.

There are currently two main types of pharmaceutical therapy for the treatment of osteoporosis and skeletal fractures. The first is the use of anti-resorptive compounds to inhibit the resorption of bone tissue and therefore prevent bone loss and reduce the incidence of skeletal fractures.

Estrogen is an example of an anti-resorptive agent. It is known that estrogen prevents post-menopausal bone loss and reduces skeletal fractures. However, estrogen fails to restore bone to the established osteoporotic skeleton. Furthermore, long-term estrogen therapy, however, has been implicated in a variety of disorders, including an increase in the risk of uterine cancer, endometrial cancer and possibly breast cancer, causing many women to avoid this treatment. The significant undesirable effects associated with estrogen therapy support the need to develop alternative therapies for osteoporosis.

A second type of pharmaceutical therapy for the treatment of osteoporosis and bone fractures is the use of anabolic agents to promote bone formation and increase bone mass. This class of agents are expected to restore bone to the established osteoporotic skeleton. There are a variety of natural prostaglandins (e.g., PGE, PGD and PGF) that are implicated in skeletal metabolism. PGE2 has been reported to stimulate bone formation, increase bone mass and bone strength in animal models of osteoporosis when administered locally or systemically. However, there are severe side effects which are associated with PGE2 such as diarrhea, gastrointestinal bleeding, decreased food consumption, dehydration, weight loss and decreased physical activity. Accordingly, PGE2 has not found widespread use in humans because of these side effects.

Recently, four different subtypes of PGE2 receptors (EP1, EP2, EP3 and EP4) have been cloned (Funk, C. D., et al., *Cloning and Expression of a cDNA for the Human Prostaglandin E Receptor EP1 Subtype,* Journal of Biological Chemistry, vol. 268, No. 35, pp. 26767–26772, 1993; Regan, J. W., et al., *Cloning of a Novel Human Prostaglandin Receptor with Characteristics of the Pharmacologically Defined EP2 Subtype,* Molecular Pharmacology, vol. 46, pp. 213–220, 1994; Yang, J., et al., *Cloning and Expression of the EP3-Subtype of Human Receptors for Prostaglandin E2,* Biochemical Biophysical Research Communication, vol. 198, pp. 999–1006, 1994; Bastien, L., et al., *Cloning, Functional Expression and Characterization of the Human Prostaglandin E2 Receptor EP2 Subtype,* Journal Biological Chemistry, vol. 269, pp. 11873–11877, 1994). J. Bone Miner. Res. 1996, 11(supp.):S174 discussed the different subtyes of the PGE2 receptors. However, it is unclear whether one or more or these PGE2 receptor subtypes is selectively associated with bone anabolism of PGE2.

Skeletal disorders are highly prevalent diseases caused by nutrition deficiency, sex steroid deficiency, aging, trauma or other factors. All approved therapies and clinically advanced candidates including calcitonin, estrogen replacement therapy, bisphosphonates and estrogen agonists act to prevent bone loss by inhibiting bone resorption, but these agents cannot restore bone mass. Thus, there is significant medical need for anabolic agents that would increase bone mass and strength above a critical threshold in established osteoporotic patients, fractured patients, and other skeletal disorder patients.

SUMMARY OF THE INVENTION

This invention is directed to a method for augmenting bone mass and preventing bone loss in a mammal (including humans) comprising selectively agonizing, one of the prostaglandin $E_2$ receptor subtypes, the EP2 receptor subtype by administering to a mammal a therapeutically effective amount of a selective EP2 receptor subtype agonist.

This invention is also directed to a method for treating (e.g., preventing) a mammal having a condition which presents with low bone mass comprising selectively agonizing the EP2 receptor subtype by administering to a mammal having a condition which presents with low bone mass a therapeutically effective amount of a selective EP2 receptor subtype agonist.

Yet another aspect of this invention is directed to methods for treating (e.g., preventing) osteoporosis, bone fractures, osteotomy, bone loss associated with periodontitis, prosthetic ingrowth, or inducing vertebral synostosis in a mammal (including a human being) by selectively agonizing the EP2 receptor subtype by administering to a mammal suffering from osteoporosis, bone fractures, osteotomy, bone loss associated with periodontitis, prosthetic ingrowth or vertebral synostosis a therapeutically effective amount of a selective EP2 receptor subtype agonist.

Yet another aspect of this invention is directed to a method for treating (e.g., preventing) osteoporosis in a mammal (including a human being) by selectively agonizing the EP2 receptor subtype by administering to a mammal suffering from osteoporosis a therapeutically effective amount of a selective EP2 receptor subtype agonist.

Yet another aspect of this invention is directed to a method for treating (e.g., preventing) osteotomy bone loss in a mammal (including a human being) by selectively agonizing the EP2 receptor subtype by administering to a mammal suffering from an osteotomy bone loss a therapeutically effective amount of a selective EP2 receptor subtype agonist.

Yet another aspect of this invention is directed to a method for treating (e.g., preventing) alveolar bone loss in a mammal (including a human being) by selectively agonizing the EP2 receptor subtype by administering to a mammal suffering from an alveolar bone loss a therapeutically effective amount of a selective EP2 receptor subtype agonist.

Yet another aspect of this invention is directed to a method for treating (e.g., preventing) bone loss associated with periodontitis in a mammal (including a human being) by selectively agonizing the EP2 receptor subtype by administering to a mammal suffering from bone loss associated with periodontitis a therapeutically effective amount of a selective EP2 receptor subtype agonist.

Yet another aspect of this invention is directed to a method for treating (e.g., preventing) childhood idiopathic bone loss in a child by selectively agonizing the EP2 receptor subtype by administering to a child suffering from childhood idiopathic bone loss a therapeutically effective amount of a selective EP2 receptor subtype agonist.

Yet another aspect of this invention is directed to a method for treating (e.g., preventing) "secondary osteoporosis", which includes glucocorticoid-induced osteoporosis, hyperthyroidism-induced osteoporosis, immobilization-induced osteoporosis, heparin-induced osteoporosis or immunosuppressive-induced osteoporosis in a mammal (including a human being) by selectively agonizing the EP2 receptor subtype by administering to a mammal suffering from "secondary osteoporosis" a therapeutically effective amount of a selective EP2 receptor subtype agonist.

Yet another aspect of this invention is directed to a method for treating (e.g., preventing) glucocorticoid-induced osteoporosis in a mammal (including a human being) by selectively agonizing the EP2 receptor subtype by administering to a mammal suffering from glucocorticoid-induced osteoporosis a therapeutically effective amount of a selective EP2 receptor subtype agonist.

Yet another aspect of this invention is directed to a method for treating (e.g., preventing) hyperthyroidism-induced osteoporosis in a mammal (including a human being) by selectively agonizing the EP2 receptor subtype by administering to a mammal suffering from hyperthyroidism-induced osteoporosis a therapeutically effective amount of a selective EP2 receptor subtype agonist.

Yet another aspect of this invention is directed to a method for treating (e.g., preventing) immobilization-induced osteoporosis in a mammal (including a human being) by selectively agonizing the EP2 receptor subtype by administering to a mammal suffering from immobilization-induced osteoporosis a therapeutically effective amount of a selective EP2 receptor subtype agonist.

Yet another aspect of this invention is directed to a method for treating (e.g., preventing) heparin-induced osteoporosis in a mammal (including a human being) by selectively agonizing the EP2 receptor subtype by administering to a mammal suffering from heparin-induced osteoporosis a therapeutically effective amount of a selective EP2 receptor subtype agonist.

Yet another aspect of this invention is directed to a method for treating (e.g., preventing) immunosuppressive-induced osteoporosis in a mammal (including a human being) by selectively agonizing the EP2 receptor subtype by administering to a mammal suffering from immunosuppressive-induced osteoporosis a therapeutically effective amount of a selective EP2 receptor subtype agonist.

Yet another aspect of this invention is directed to a method for enhancing bone fracture healing in a mammal (including a human being) by selectively agonizing the EP2 receptor subtype by administering to a mammal suffering from a bone fracture a therapeutically effective amount of a selective EP2 receptor subtype agonist. In one aspect of this invention the agonist is applied locally to the site of bone fracture.

Yet another aspect of this invention is directed to a method for enhancing bone healing following facial reconstruction or maxillary reconstruction or mandibular reconstruction in a mammal (including a human being) by selectively agonizing the EP2 receptor subtype by administering to a mammal which has undergone facial reconstruction or maxillary reconstruction or mandibular reconstruction a therapeutically effective amount of a selective EP2 receptor subtype agonist. In one aspect of this invention the agonist is applied locally to the site of bone reconstruction.

Yet another aspect of this invention is directed to a method for treating prosthetic ingrowth in a mammal (including a human being) by selectively agonizing the EP2 receptor subtype by administering to a mammal suffering from for prosthetic ingrowth a therapeutically effective amount of a selective EP2 receptor subtype agonist.

Yet another aspect of this invention is directed to a method for inducing vertebral synostosis in a mammal (including a human being) by selectively agonizing the EP2 receptor subtype by administering to a mammal undergoing surgery for vertebral synostosis a therapeutically effective amount of a selective EP2 receptor subtype agonist.

Yet another aspect of this invention is directed to a method for enhancing long bone extension in a mammal (including a human being) by selectively agonizing the EP2 receptor subtype by administering to a mammal suffering from an insufficiently sized long bone a therapeutically effective amount of a selective EP2 receptor subtype agonist.

Yet another aspect of this invention is directed to a method for treating a bone graft in a mammal (including a human being) by selectively agonizing the EP2 receptor subtype by administering to a mammal suffering from a bone graft a therapeutically effective amount of a selective EP2 receptor subtype agonist. In one aspect of this invention the agonist is applied locally to the site of the bone graft.

Preferably post-menopausal women and men over the age of 60 are treated.

In a preferred mode the EP2 agonist is at least 10 fold selective for the EP2 receptor subtype over the EP1, EP3 and EP4 receptor subtypes.

In a preferred mode the EP2 agonist is at least 25 fold selective for the EP2 receptor subtype over the EP1, EP3 and EP4 receptor subtypes.

In a preferred mode the EP2 agonist is at least 50 fold selective for the EP2 receptor subtype over the EP1, EP3 and EP4 receptor subtypes.

In a preferred mode the EP2 agonist is at least 75 fold selective for the EP2 receptor subtype over the EP1, EP3 and EP4 receptor subtypes.

In an especially preferred mode the EP2 agonist is at least 100 fold selective for the EP2 receptor subtype over the EP1, EP3 and EP4 receptor subtypes.

In an especially preferred mode the EP2 agonist is at least 150 fold selective for the EP2 receptor subtype over the EP1, EP3 and EP4 receptor subtypes.

In an especially preferred mode the EP2 agonist is at least 200 fold selective for the EP2 receptor subtype over the EP1, EP3 and EP4 receptor subtypes.

In an especially preferred mode the EP2 agonist is at least 250 fold selective for the EP2 receptor subtype over the EP1, EP3 and EP4 receptor subtypes.

In an especially preferred mode the EP2 agonist is at least 300 fold selective for the EP2 receptor subtype over the EP1, EP3 and EP4 receptor subtypes.

A preferred dosage is about 0.001 to 100 mg/kg/day of the selective EP2 agonist. An especially preferred dosage is about 0.01 to 50 mg/kg/day of the EP2 agonist.

Preferred selective EP2 agonists are compounds of Formula I

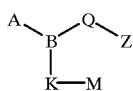

Formula I or a pharmaceutically-acceptable salt or prodrug thereof wherein either (i):

B is N;

A is $(C_1-C_6)$alkylsulfonyl, $(C_3-C_7)$cycloalkylsulfonyl, $(C_3-C_7)$cycloalkyl$(C_1-C_6)$alkylsulfonyl, said A moieties optionally mono-, di- or tri- substituted on carbon independently with hydroxy, $(C_1-C_4)$alkyl or halo;

Q is

—$(C_2-C_6)$alkylene-W—$(C_1-C_3)$alkylene-,

—$(C_3-C_8)$alkylene-, said —$(C_3-C_8)$alkylene- optionally substituted with up to four substituents independently selected from fluoro or $(C_1-C_4)$alkyl, —X—$(C_1-C_5)$alkylene-, —$(C_1-C_5)$alkylene-X—, —$(C_1-C_3)$alkylene-X—$(C_1-C_3)$alkylene-, —$(C_2-C_4)$alkylene-W—X—$(C_0-C_3)$alkylene-, —$(C_0-C_4)$alkylene-X—W—$(C_1-C_3)$alkylene-, —$(C_2-C_5)$alkylene-W—X—W—$(C_1-C_3)$alkylene-, wherein the two occurrences of W are independent of each other, —$(C_1-C_4)$alkylene-ethenylene-$(C_1-C_4)$alkylene-, —$(C_1-C_4)$alkylene-ethenylene-$(C_0-C_2)$alkylene-X—$(C_0-C_5)$alkylene-, —$(C_1-C_4)$alkylene-ethenylene-$(C_0-C_2)$alkylene-X—W—$(C_1-C_3)$alkylene-, —$(C_1-C_4)$alkylene-ethynylene-$(C_1-C_4)$alkylene-, or —$(C_1-C_4)$alkylene-ethynylene-X—$(C_0-C_3)$alkylene-;

W is oxy, thio, sulfino, sulfonyl, aminosulfonyl-, -mono-N—$(C_1-C_4)$alkyleneaminosulfonyl-, sulfonylamino, N—$(C_1-C_4)$alkylenesulfonylamino, carboxamido, N—$(C_1-C_4)$alkylenecarboxamido, carboxamidooxy, N—$(C_1-C_4)$alkylenecarboxamidooxy, carbamoyl, -mono-N—$(C_1-C_4)$alkylenecarbamoyl, carbamoyloxy, or -mono-N—$(C_1-C_4)$alkylenecarbamoyloxy, wherein said W alkyl groups are optionally substituted on carbon with one to three fluorines;

X is a five or six membered aromatic ring optionally having one or two heteroatoms selected independently from oxygen, nitrogen, and sulfur; said ring optionally mono-, or di-substituted independently with halo, $(C_1-C_3)$alkyl, trifluoromethyl, trifluoromethyloxy, difluoromethyloxy, hydroxyl, $(C_1-C_4)$alkoxy, or carbamoyl;

Z is carboxyl, $(C_1-C_6)$alkoxycarbonyl, tetrazolyl, 1,2,4-oxadiazolyl, 5-oxo-1,2,4-oxadiazolyl, $(C_1-C_4)$alkylsulfonylcarbamoyl or phenylsulfonylcarbamoyl;

K is a bond, $(C_1-C_8)$alkylene, thio$(C_1-C_4)$alkylene or oxy$(C_1-C_4)$alkylene, said $(C_1-C_8)$alkylene optionally mono-unsaturated and wherein K is optionally mono-, di- or tri-substituted independently with fluoro, methyl or chloro;

M is —Ar, —Ar$^1$—V—Ar$^2$, —Ar$^1$—S—Ar$^2$ or —Ar$^1$—O—Ar$^2$ wherein Ar, Ar$^1$ and Ar$^2$ are each independently a partially saturated, fully saturated or fully unsaturated five to eight membered ring optionally having one to four heteroatoms selected independently from oxygen, sulfur and nitrogen, or, a bicyclic ring consisting of two fused partially saturated, fully saturated or fully unsaturated five or six membered rings, taken independently, optionally having one to four heteroatoms selected independently from nitrogen, sulfur and oxygen;

said Ar, Ar$^1$ and Ar$^2$ moieties optionally substituted, on one ring if the moiety is monocyclic, or one or both rings if the moiety is bicyclic, on carbon with up to three substituents independently selected from R$^1$, R$^2$ and R$^3$ wherein R$^1$, R$^2$ and R$^3$ are hydroxy, nitro, halo, $(C_1-C_6)$alkoxy, $(C_1-C_4)$alkoxy$(C_1-C_4)$alkyl, $(C_1-C_4)$alkoxycarbonyl, $(C_1-C_7)$alkyl, $(C_3-C_7)$cycloalkyl, $(C_3-C_7)$cycloalkyl$(C_1-C_4)$alkyl, $(C_3-C_7)$cycloalkyl$(C_1-C_4)$alkanoyl, formyl, $(C_1-C_8)$alkanoyl, $(C_1-C_6)$alkanoyl$(C_1-C_6)$alkyl, $(C_1-C_4)$alkanoylamino, $(C_1-C_4)$alkoxycarbonylamino, sulfonamido, $(C_1-C_4)$alkylsulfonamido, amino, mono-N— or di-N,N—$(C_1-C_4)$alkylamino, carbamoyl, mono- N— or di-N,N—$(C_1-C_4)$alkylcarbamoyl, cyano, thiol, $(C_1-C_6)$alkylthio, $(C_1-C_6)$alkylsulfinyl, $(C_1-C_4)$alkylsulfonyl or mono-N- or di-N,N—$(C_1-C_4)$alkylaminosulfinyl;

R$^1$, R$^2$ and R$^3$ are optionally mono-, di- or tri-substituted on carbon independently with halo or hydroxy; and V is a bond or $(C_1-C_3)$alkylene optionally mono- or di-substituted independently with hydroxy or fluoro with the proviso that when K is $(C_2-C_4)$alkylene and M is Ar and Ar is cyclopent-1-yl, cyclohex-1-yl, cyclohept-1-yl or cyclooct-1-yl then said $(C_5-C_8)$cycloalkyl substituents are not substituted at the one position with hydroxy; or (ii):

B is N;

A is $(C_1-C_6)$alkanoyl, or $(C_3-C_7)$cycloalkyl$(C_1-C_6)$alkanoyl, said A moieties optionally mono-, di- or tri-substituted independently on carbon with hydroxy or halo;

Q is

—$(C_2-C_6)$alkylene-W—$(C_1-C_3)$alkylene-,

—$(C_4-C_8)$alkylene-, said —$(C_4-C_8)$alkylene- optionally substituted with up to four substituents independently selected from fluoro or $(C_1-C_4)$alkyl, —X—$(C_2-C_5)$alkylene-, —$(C_1-C_5)$alkylene-X—, —$(C_1-C_3)$alkylene-X—$(C_1-C_3)$alkylene-, —($C_2$–$C_4$)alkylene-W—X—($C_0$–$C_3$)alkylene-,
—($C_0$–$C_4$)alkylene-X—W—($C_1$–$C_3$)alkylene-,
—($C_2$–$C_5$)alkylene-W—X—W—($C_1$–$C_3$)alkylene-, wherein the two occurrences of W are independent of each other,
—($C_1$–$C_4$)alkylene-ethenylene-($C_1$–$C_4$)alkylene-,
—($C_1$–$C_4$)alkylene-ethenylene-($C_0$–$C_2$)alkylene-X—($C_0$–$C_5$)alkylene-,
—($C_1$–$C_4$)alkylene-ethenylene-($C_0$–$C_2$)alkylene-X—W—($C_1$–$C_3$)alkylene-,
—($C_1$–$C_4$)alkylene-ethynylene-($C_1$–$C_4$)alkylene-, or
—($C_1$–$C_4$)alkylene-ethynylene-X—($C_0$–$C_3$)alkylene-;

W is oxy, thio, sulfino, sulfonyl, aminosulfonyl-, -mono-N—($C_1$–$C_4$)alkyleneaminosulfonyl-, sulfonylamino, N—($C_1$–$C_4$)alkylenesulfonylamino, carboxamido, N—($C_1$–$C_4$)alkylenecarboxamido, carboxamidooxy, N—($C_1$–$C_4$)alkylenecarboxamidooxy, carbamoyl, -mono-N—($C_1$–$C_4$)alkylenecarbamoyl, carbamoyloxy, or -mono-N—($C_1$–$C_4$)alkylenecarbamoyloxy, wherein said W alkyl groups are optionally substituted on carbon with one to three fluorines;

X is a five or six membered aromatic ring optionally having one or two heteroatoms independently selected from oxygen, nitrogen, and sulfur; said ring optionally mono-, or di-substituted independently with halo, ($C_1$–$C_3$)alkyl, trifluoromethyl, trifluoromethyloxy, difluoromethyloxy, hydroxyl, ($C_1$–$C_4$)alkoxy, or carbamoyl;

Z is carboxyl, ($C_1$–$C_6$)alkoxycarbonyl, tetrazolyl, 1,2,4-oxadiazolyl, 5-oxo-1,2,4-oxadiazolyl, ($C_1$–$C_4$) alkylsulfonylcarbamoyl or phenylsulfonylcarbamoyl;

K is ($C_1$–$C_8$)alkylene, thio($C_1$–$C_4$)alkylene or oxy($C_1$–$C_4$)alkylene, said ($C_1$–$C_8$)alkylene optionally mono-unsaturated and wherein K is optionally mono-, di- or tri- substituted independently with fluoro, methyl or chloro;

M is —Ar, —$Ar^1$—V—$A^2$, —$Ar^1$—S—$Ar^2$ or —$Ar^1$—O—$A^2$ wherein Ar, $Ar^1$ and $Ar^2$ are each independently a partially saturated, fully saturated or fully unsaturated five to eight membered ring optionally having one to four heteroatoms selected independently from oxygen, sulfur and nitrogen, or, a bicyclic ring consisting of two fused partially saturated, fully saturated or fully unsaturated five or six membered rings, taken independently, optionally having one to four heteroatoms selected independently from nitrogen, sulfur and oxygen;

said Ar, $Ar^1$ and $Ar^2$ moieties optionally substituted, on one ring if the moiety is monocyclic, or one or both rings if the moiety is bicyclic, on carbon with up to three substituents independently selected from $R^1$, $R^2$ and $R^3$ wherein $R^1$, $R^2$ and $R^3$ are H, hydroxy, nitro, halo, ($C_1$–$C_6$)alkoxy, ($C_1$–$C_4$)alkoxy($C_1$–$C_4$)alkyl, ($C_1$–$C_4$)alkoxycarbonyl, ($C_1$–$C_7$)alkyl, ($C_3$–$C_7$)cycloalkyl, ($C_3$–$C_7$)cycloalkyl($C_1$–$C_4$)alkyl, ($C_3$–$C_7$)cycloalkyl($_1$–$C_4$)alkanoyl, formyl, ($C_1$–$C_8$)alkanoyl, ($C_1$–$C_6$)alkanoyl($C_1$–$C_6$)alkyl, ($C_1$–$C_4$)alkanoylamino, ($C_1$–$C_4$)alkoxycarbonylamino, sulfonamido, ($C_1$–$C_4$) alkylsulfonamido, amino, mono-N— or di-N,N—($C_1$–$C_4$)alkylamino, carbamoyl, mono- N— or di-N, N—($C_1$–$C_4$)alkylcarbamoyl, cyano, thiol, ($C_1$–$C_6$) alkylthio, ($C_1$–$C_6$)alkylsulfinyl, ($C_1$–$C_4$)alkylsulfonyl or mono-N— or di-N,N—($C_1$–$C_4$)alkylaminosulfinyl;

$R^1$, $R^2$ and $R^3$ are optionally mono-, di- or tri-substituted on carbon independently with halo or hydroxy; and V is a bond or ($C_1$–$C_3$)alkylene optionally mono- or di-substituted independently with hydroxy or fluoro with the proviso that when K is ($C_2$–$C_4$)alkylene and M is Ar and Ar is cyclopent-1-yl, cyclohex-1-yl, cyclohept-1-yl or cycloct-1-yl then said ($C_5$–$C_8$) cycloalkyl substituents are not substituted at the one position with hydroxy and with the proviso that 6-[(3-Phenyl-propyl)-(2-propyl-pentanoyl)-amino]-hexanoic acid and its ethyl ester are not included or (iii):

B is C(H);

A is ($C_1$–$C_6$)alkanoyl, or ($C_3$–$C_7$)cycloalkyl($C_1$–$C_6$) alkanoyl, said A moieties optionally mono-, di- or tri-substituted on carbon independently with hydroxy or halo;

Q is
—($C_2$–$C_6$)alkylene-W—($C_1$–$C_3$)alkylene-,
—($C_4$–$C_8$)alkylene-, said -($C_4$–$C_8$)alkylene- optionally substituted with up to four substituents independently selected from fluoro or ($C_1$–$C_4$)alkyl,
—X—($C_1$–$C_5$)alkylene-,
—($C_1$–$C_5$)alkylene-X—,
—($C_1$–$C_3$)alkylene-X—($C_1$–$C_3$)alkylene-,
—($C_2$–$C_4$)alkylene-W—X—($C_0$–$C_3$)alkylene-,
—($C_0$–$C_4$)alkylene-X—W—($C_1$–$C_3$)alkylene-,
—($C_2$–$C_5$)alkylene-W—X—W—($C_1$–$C_3$)alkylene-, wherein the two occurrences of W are independent of each other,
—($C_1$–$C_4$)alkylene-ethenylene-($C_1$–$C_4$)alkylene-,
—($C_1$–$C_4$)alkylene-ethenylene-($C_0$–$C_2$)alkylene-X—($C_0$–$C_5$)alkylene-,
—($C_1$–$C_4$)alkylene-ethenylene-($C_0$–$C_2$)alkylene-X—W—($C_1$–$C_3$)alkylene-,
—($C_1$–$C_4$)alkylene-ethynylene-($C_1$–$C_4$)alkylene-, or
—($C_1$–$C_4$)alkylene-ethynylene-X—($C_0$–$C_3$)alkylene-;

W is oxy, thio, sulfino, sulfonyl, aminosulfonyl-, -mono-N—($C_1$–$C_4$)alkyleneaminosulfonyl-, sulfonylamino, N—($C_1$–$C_4$)alkylenesulfonylamino, carboxamido, N—($C_1$–$C_4$)alkylenecarboxamido, carboxamidooxy, N—($C_1$–$C_4$)alkylenecarboxamidooxy, carbamoyl, -mono-N—($C_1$–$C_4$)alkylenecarbamoyl, carbamoyloxy, or -mono-N—($C_1$–$C_4$)alkylenecarbamoyloxy, wherein said W alkyl groups are optionally substituted on carbon with one to three fluorines;

X is a five or six membered aromatic ring optionally having one or two heteroatoms selected independently from oxygen, nitrogen and sulfur; said ring optionally mono-, or di-substituted independently with halo, ($C_1$–$C_3$)alkyl, trifluoromethyl, trifluoromethyloxy, difluoromethyloxy, hydroxyl, ($C_1$–$C_4$)alkoxy, or carbamoyl;

Z is carboxyl, ($C_1$–$C_6$)alkoxycarbonyl, tetrazolyl, 1,2,4-oxadiazolyl, 5-oxo-1,2,4—oxadiazolyl, ($C_1$–$C_4$) alkylsulfonylcarbamoyl or phenylsulfonylcarbamoyl;

K is a bond, ($C_1$–$C_8$)alkylene, thio($C_1$–$C_4$)alkylene, ($C_4$–$C_7$)cycloalkyl($C_1$–$C_6$)alkylene or oxy($C_1$–$C_4$) alkylene, said ($C_1$–$C_8$)alkylene optionally mono-unsaturated and wherein K is optionally mono-, di- or tri-substituted independently with fluoro, methyl or chloro;

M is —Ar, —$Ar^1$—V—$Ar^2$, —$Ar^1$—S—$Ar^2$ or —$Ar^1$—O—$Ar^2$ wherein Ar, $Ar^1$ and $Ar^2$ are each independently a partially saturated, fully saturated or fully unsaturated five to eight membered ring optionally having one to four heteroatoms selected independently from oxygen, sulfur and nitrogen, or, a bicyclic ring consisting of two fused partially saturated, fully saturated or fully unsaturated five or six membered rings, taken independently, optionally having one to four heteroatoms selected independently from nitrogen, sulfur and oxygen;

said Ar, $Ar^1$ and $Ar^2$ moieties optionally substituted, on one ring if the moiety is monocyclic, or one or both rings if the moiety is bicyclic, on carbon with up to three substituents independently selected from $R^1$, $R^2$ and $R^3$ wherein $R^1$, $R^2$ and $R^3$ are H, hydroxy, nitro, halo, $(C_1-C_6)$alkoxy, $(C_1-C_4)$alkoxy$(C_1-C_4)$alkyl, $(C_1-C_4)$alkoxycarbonyl, $(C_1-C_7)$alkyl, $(C_3-C_7)$cycloalkyl, $(C_3-C_7)$cycloalkyl$(C_1-C_4)$alkyl, $(C_3-C_7)$cycloalkyl$(C_1-C_4)$alkanoyl, formyl, $(C_1-C_8)$alkanoyl, $(C_1-C_6)$alkanoyl$(C_1-C_6)$alkyl, $(C_1-C_4)$alkanoylamino, $(C_1-C_4)$alkoxycarbonylamino, sulfonamido, $(C_1-C_4)$alkylsulfonamido, amino, mono-N- or di-N,N—$(C_1-C_4)$alkylamino, carbamoyl, mono-N— or di-N,N—$(C_1-C_4)$alkylcarbamoyl, cyano, thiol, $(C_1-C_6)$alkylthio, $(C_1-C_6)$alkylsulfinyl, $(C_1-C_4)$alkylsulfonyl or mono-N— or di-N,N—$(C_1-C_4)$alkylaminosulfinyl;

$R^1$, $R^2$ and $R^3$ are optionally mono-, di- or tri-substituted independently on carbon with halo or hydroxy; and V is a bond or $(C_1-C_3)$alkylene optionally mono- or di-substituted independently with hydroxy or fluoro with the proviso that when K is $(C_2-C_4)$alkylene and M is Ar and Ar is cyclopent-1-yl, cyclohex-1-yl, cyclohept-1-yl or cyclooct-1-yl then said $(C_5-C_8)$cycloalkyl substituents are not substituted at the one position with hydroxy.

A preferred group of compounds, designated the A Group, contains those compounds having the Formula I as shown above wherein B is N;

A is $(C_1-C_6)$alkylsulfonyl, $(C_3-C_6)$cycloalkylsulfonyl or $(C_3-C_6)$cycloalkyl$(C_1-C_6)$alkylsulfonyl, said A moieties optionally mono-, di-, or tri-substituted on carbon with fluoro;

X is phenyl, thienyl, or thiazolyl said phenyl, thienyl or thiazolyl optionally mono- or di-substituted independently with fluoro, chloro, trifluoromethyl, methoxy, difluoromethoxy or trifluoromethoxy;

W is oxy, thio or sulfonyl;

Z is carboxyl, $(C_1-C_4)$alkoxycarbonyl or tetrazolyl;

K is methylene or ethylene;

Ar, $Ar^1$ and $Ar^2$ are each independently $(C_5-C_7)$cycloalkyl, phenyl, thienyl, thiazolyl, pyridyl, pyrimidyl, oxazolyl, furanyl, imidazolyl, isoxazolyl, pyrazinyl or pyrazolyl;

$R^1$ is halo, $(C_1-C_6)$alkoxy, $(C_1-C_7)$alkyl, $(C_3-C_7)$cycloalkyl, or $(C_3-C_7)$cycloalkyl$(C_1-C_4)$alkyl, said $(C_1-C_6)$alkoxy, $(C_1-C_7)$alkyl, $(C_3-C_7)$cycloalkyl or $C_3-C_7)$cycloalkyl$(C_1-C_4)$alkyl, optionally mono-, di- or tri-substituted independently with hydroxy, fluoro or chloro; and $R^2$ and $R^3$ are chloro, fluoro, methyl, methoxy, difluoromethoxy, trifluoromethoxy or trifluoromethyl.

A group of compounds which is preferred among the A Group of compounds designated the B Group, contains those compounds wherein A is $(C_1-C_3)$alkylsulfonyl;

Q is

—$(C_2-C_6)$alkylene-W—$(C_1-C_3)$alkylene-,

—$(C_4-C_8)$alkylene-, said —$(C_4-C_8)$alkylene- optionally substituted with up to four substituents independently selected from fluoro or $(C_1-C_4)$alkyl, —X—$(C_2-C_5)$alkylene-, —$(C_1-C_5)$alkylene-X—, —$(C_1-C_3)$alkylene-X—$(C_1-C_3)$alkylene-, —$(C_2-C_4)$alkylene-W—X—$(C_0-C_3)$alkylene-, or —$(C_0-C_4)$alkylene-X—W—$(C_1-C_3)$alkylene-;

M is —$Ar^1$—V—$Ar^2$ or —$Ar^1$—O—$Ar^2$ wherein $Ar^1$ and $Ar^2$ are each independently phenyl, pyridyl or thienyl;

V is a bond or $(C_1-C_2)$alkylene;

$R^1$ is chloro, fluoro, $(C_1-C_4)$alkyl or $(C_1-C_4)$alkoxy, said $(C_1-C_4)$alkyl and $(C_1-C_4)$alkoxy optionally mono-, di- or tri-substituted independently with hydroxy or fluoro; and $R^2$ and $R^3$ are each independently chloro or fluoro.

Especially preferred compounds within the B Group of compounds are

7-[(2'-Hydroxymethyl-biphenyl-4-ylmethyl)-methanesulfonyl-amino)-heptanoic acid, 7-{[4-(3-Hydroxymethyl-thiophen-2-yl)-benzyl]-methanesulfonyl-amino}-heptanoic acid, and 7-[(2'-Chloro-biphenyl4-ylmethyl)-methanesulfonyl-amino]-heptanoic acid.

Especially preferred compounds within the B Group of compounds are compounds wherein a. A is methylsulfonyl;

Q is n-hexylene;

Z is carboxyl;

K is methylene; and

M is 4-(2-hydroxymethylphenyl)phenyl;

b. A is methylsulfonyl;

Q is n-hexylene;

Z is carboxyl;

K is methylene; and

M is 4-(3-hydroxymethylthien-2-yl)phenyl; and c. A is methylsulfonyl;

Q is n-hexylene;

Z is carboxyl;

K is methylene; and

M is 4-(2-chlorophenyl)phenyl.

A preferred group of compounds, designated the C Group, contains those compounds having the Formula I as shown above wherein B is N;

A is $(C_1-C_6)$alkylsulfonyl, $(C_3-C_6)$cycloalkylsulfonyl, $(C_3-C_6)$cycloalkyl$(C_1-C_6)$alkylsulfonyl;

X is phenyl, thienyl, or thiazolyl said phenyl, thienyl or thiazolyl optionally mono- or di-substituted independently with fluoro, chloro, trifluoromethyl, methoxy, difluoromethoxy or trifluoromethyloxy;

W is oxy, thio or sulfonyl;

Z is carboxyl, $(C_1-C_4)$alkoxycarbonyl or tetrazolyl;

K is $(C_1-C_8)$alkylene or oxy$(C_1-C_4)$alkylene, said $(C_1-C_8)$alkylene optionally mono-unsaturated and wherein K is optionally mono-, di- or tri-substituted independently with methyl, fluoro or chloro;

M is —Ar, said —Ar is phenyl, thienyl, pyridyl, thiazolyl, oxazolyl, isoxazolyl, naphthalenyl, benzo[b]furanyl, benzo[b]thiophenyl, indanyl, furanyl, benzo[1,3]dioxolyl, benzimidazolyl, benzisoxazolyl, 2,3- dihydrobenzo[1,4]dioxinyl, 2,3-dihydrobenzofuranyl, pyrazolyl, pyrimidyl, imidazolyl, quinolinyl, isoquinolinyl, benzoxazolyl, benzothiazolyl, indolyl, 1,2,3,4-tetrahydronaphthalenyl, cyclohexyl, cyclopentyl, cyclobutyl, cycloheptyl or chromanyl;

$R^1$ is halo, $(C_1-C_6)$alkoxy, $(C_1-C_7)$alkyl, $(C_3-C_7)$ cycloalkyl, $(C_1-C_7)$alkanoyl or $(C_3-C_7)$cycloalkyl $(C_1-C_4)$alkyl, said $(C_1-C_6)$alkoxy, $(C_1-C_7)$alkyl, $(C_3-C_7)$cycloalkyl, $(C_1-C_7)$alkanoyl or $(C_3-C_7)$ cycloalkyl$(C_1-C_4)$alkyl, optionally mono-, di- or tri-substituted independently with hydroxy, fluoro or chloro; and $R^2$ and $R^3$ are each independently hydroxy, halo, trifluoromethyl, $(C_1-C_7)$alkyl, $(C_1-C_4)$alkoxy, $(C_1-C_5)$ alkanoyl, cyano, $(C_3-C_7)$cycloalkyl, $(C_3-C_7)$ cycloalkyl$(C_1-C_4)$alkyl, formyl, difluoromethoxy, trifluoromethoxy or carbamoyl.

It is especially preferred for Group C compounds that K is not optionally mono-, di- or tri-substituted independently with methyl, fluoro or chloro.

A group of compounds which is preferred among the C Group of compounds, designated the D Group, contains those compounds wherein K is methylene;

A is $(C_1-C_3)$alkylsulfonyl;

M is —Ar and —Ar is phenyl, thiazolyl, pyridyl, thienyl, oxazolyl, furanyl, cyclopentyl or cyclohexyl wherein —Ar is substituted with at least $R^1$;

$R^1$ is $(C_1-C_7)$alkyl or $(C_1-C_5)$alkoxy, said $(C_1-C_7)$alkyl or $(C_1-C_5)$alkoxy optionally mono-, di- or tri-substituted independently with hydroxy or fluoro; and $R^2$ and $R^3$ are each independently chloro, fluoro, methyl, difluoromethoxy, trifluoromethoxy or trifluoromethyl.

Especially preferred among the D Group of compounds are

7-{[4-(1-Hydroxy-hexyl)-benzyl]-methanesulfonyl-amino]-heptanoic acid,

7-[(4-Butyl-benzyl)-methanesulfonyl-amino]-heptanoic acid,

7-{[5-(1-Hydroxy-hexyl)-thiophen-2-ylmethyl]-methanesulfonyl-amino}-heptanoic acid and (3-{[(4-Butyl-benzyl)-methanesulfonyl-amino]-methyl}-phenyl)-acetic acid.

A group of compounds which is preferred among the D Group of compounds, designated the E Group, contains those compounds wherein Q is —$(C_2-C_6)$alkylene-W—$(C_1-C_3)$alkylene-; and W is oxy.

A group of compounds which is preferred among the D Group of compounds, designated the F Group, contains those compounds wherein Q is —$(C_3-C_8)$alkylene-, said —$(C_3-C_8)$alkylene- optionally substituted with from one to four fluorines.

Especially preferred compounds among the F Group of compounds are compounds wherein a.
A is methylsulfonyl;
Q is n-hexylene;
Z is carboxyl;
K is methylene; and
M is 4-(1-hydroxy-n-hexylene-1-yl)phenyl;

b.
A is methylsulfonyl;
Q is n-hexylene;
Z is carboxyl;
K is methylene; and
M is 4-(n-butylene-1-yl)phenyl; and c.
A is methylsulfonyl;
Q is n-hexylene;
Z is carboxyl;
K is methylene; and
M is 5-(1-hydroxy-n-hexylene-1-yl)thien-2-yl.

A group of compounds which is preferred among the D Group of compounds, designated the G Group, contains those compounds wherein Q is —X—$(C_1-C_5)$alkylene-; and X is thienyl or phenyl; said phenyl and thienyl optionally mono- or di-substituted independently with fluoro, chloro, trifluoromethyl or methoxy.

A group of compounds which is preferred among the D Group of compounds, designated the H Group, contains those compounds wherein Q is —$(C_1-C_5)$alkylene-X—; and X is thienyl or phenyl; said phenyl and thienyl optionally mono- or di-substituted independently with fluoro, chloro, trifluoromethyl or methoxy.

A group of compounds which is preferred among the D Group of compounds, designated the I Group, contains those compounds wherein Q is —$(C_1-C_3)$alkylene-X—$(C_1-C_3)$alkylene-; and X is thienyl or phenyl; said phenyl and thienyl optionally mono- or di-substituted independently with fluoro, chloro, trifluoromethyl or methoxy.

An especially preferred compound within the I Group of compounds is a compound wherein A is methylsulfonyl;
Q is 3-methylenephenylmethyl;
Z is carboxyl;
K is methylene; and
M is 4-(n-butylene-1-yl)phenyl.

A group of compounds which is preferred among the D Group of compounds, designated the J Group, contains those compounds wherein Q is —$(C_2-C_4)$alkylene-W—X—$(C_0-C_3)$alkylene-;

X is thienyl or phenyl; said phenyl and thienyl optionally mono- or di-substituted independently with fluoro, chloro, trifluoromethyl or methoxy; and W is oxy.

A group of compounds which is preferred among the D Group of compounds, designated the K Group, contains those compounds wherein Q is —$(C_0-C_4)$alkylene-X—W—$(C_1-C_3)$alkylene-;

X is thienyl or phenyl; said phenyl and thienyl optionally mono- or di-substituted independently with fluoro, chloro, trifluoromethyl or methoxy; and W is oxy.

A group of compounds which is preferred among the D Group of compounds, designated the L Group, contains those compounds wherein Q is —$(C_2-C_4)$alkylene-W—X—W—$(C_1-C_3)$alkylene-;

W is oxy; and

X is thienyl or phenyl; said phenyl and thienyl optionally mono- or di-substituted independently with fluoro, chloro, trifluoromethyl or methoxy.

A group of compounds which is preferred among the D Group of compounds, designated the M Group, contains those compounds wherein Q is —($C_1$–$C_4$)alkylene-ethenylene-($C_1$–$C_4$)alkylene-; and M is —Ar and —Ar is phenyl, thiazolyl, pyridyl or thienyl.

A group of compounds which is preferred among the D Group of compounds, designated the N Group, contains those compounds wherein Q is —($C_1$–$C_4$)alkylene-ethenylene-($C_0$–$C_2$)alkylene-X—($C_0$–$C_3$)alkylene-; and X is thienyl or phenyl; said phenyl and thienyl optionally mono- or di-substituted independently with fluoro, chloro, trifluoromethyl or methoxy.

A group of compounds which is preferred among the D Group of compounds, designated the O Group, contains those compounds wherein Q is —($C_1$–$C_3$)alkylene-ethenylene-($C_0$–$C_2$)alkylene-X—W—($C_1$–$C_3$)alkylene-;

W is oxy; and

X is thienyl or phenyl; said phenyl and thienyl optionally mono- or di-substituted independently with fluoro, chloro, trifluoromethyl or methoxy.

A group of compounds which is preferred among the D Group of compounds, designated the P Group, contains those compounds wherein Q is —($C_1$–$C_4$)alkylene-ethynylene-($C_1$–$C_4$)alkylene-.

A group of compounds which is preferred among the D Group of compounds designated the Q Group, contains those compounds wherein Q is —($C_1$–$C_4$)alkylene-ethynylene-X—($C_0$–$C_3$)alkylene-; and X is thienyl or phenyl; said phenyl and thienyl optionally mono- or di-substituted independently with fluoro, chloro, trifluoromethyl or methoxy.

A group of compounds which is preferred among the C Group of compounds designated the R Group, contains those compounds wherein A is ($C_1$–$C_3$)alkylsulfonyl;

K is ($C_1$–$C_8$)alkylene;

—Ar is phenyl, thiazolyl, pyridyl, thienyl, benzofuranyl, benzo[1,3]dioxolyl, 2,3-dihydrobenzo[1,4]dioxine, 2,3-dihydrobenzofuranyl, benzimidazolyl, benzo[b]thiophenyl, cyclopentyl or cyclohexyl; and $R^1$, $R^2$ and $R^3$ are each independently hydroxy, halo, trifluoromethyl, difluoromethoxy, trifluoromethoxy, ($C_1$–$C_4$)alkoxy or ($C_1$–$C_7$)alkyl.

Preferred compounds among the R Group are
7-{[3-(3-Chloro-phenyl)-propyl)-methanesulfonyl-amino}-heptanoic acid,
7-{[3-(3,5-Dichloro-phenyl)-propyl]-methanesulfonyl-amino}-heptanoic acid and
5-(3-{[3-(3-Chloro-phenyl)-propyl]-methanesulfonyl-amino}-propyl)-thiophene-2-carboxylic acid.

A group of compounds which is preferred among the R Group of compounds, designated the S Group, contains those compounds wherein Q is —($C_2$–$C_6$)alkylene-W—($C_1$–$C_3$)alkylene-; and W is oxy.

A group of compounds which is preferred among the R Group of compounds, designated the T Group, contains those compounds wherein Q is —($C_3$–$C_8$)alkylene-, said —($C_3$–$C_8$)alkylene- optionally substituted with from one to four fluorines.

Especially preferred compounds among the T Group are compounds wherein a.
A is methylsulfonyl;
Q is n-hexylene;
Z is carboxyl;
K is propylene; and
M is 3-chlorophenyl; and b.
A is methylsulfonyl;
Q is n-hexylene;
Z is carboxyl;
K is propylene; and
M is 3,5-dichlorophenyl.

A group of compounds which is preferred among the R Group of compounds, designated the U Group, contains those compounds wherein Q is —X—($C_1$–$C_5$)alkylene-; and X is thienyl or phenyl; said phenyl and thienyl optionally mono- or di-substituted independently with fluoro, chloro, trifluoromethyl or methoxy.

A group of compounds which is preferred among the R Group of compounds, designated the V Group, contains those compounds wherein Q is —($C_1$–$C_5$)alkylene-X—; and X is thienyl or phenyl; said phenyl and thienyl optionally mono- or di-substituted independently with fluoro, chloro, trifluoromethyl or methoxy.

An especially preferred compound among the V group is a compound wherein

A is methylsulfonyl;
Q—Z is 3-(2-carboxylthien-5-yl)-n-propylene
K is propylene; and
M is 3-chlorophenyl.

A group of compounds which is preferred among the R Group of compounds, designated the W Group, contains those compounds wherein Q is -($C_1$–$C_3$)alkylene-X—($C_1$–$C_3$)alkylene-; and X is thienyl or phenyl; said phenyl and thienyl optionally mono- or di-substituted independently with fluoro, chloro, trifluoromethyl or methoxy.

A group of compounds which is preferred among the R Group of compounds, designated the X Group, contains those compounds wherein Q is —($C_2$–$C_4$)alkylene-W—X—($C_0$–$C_3$)alkylene-;

X is thienyl or phenyl; said phenyl and thienyl optionally mono- or di-substituted independently with fluoro, chloro, trifluoromethyl or methoxy; and W is oxy.

A group of compounds which is preferred among the R Group of compounds, designated the Y Group, contains those compounds wherein Q is —($C_0$–$C_4$)alkylene-X—W—($C_1$–$C_3$)alkylene-;

X is thienyl or phenyl; said phenyl and thienyl optionally mono- or di-substituted independently with fluoro, chloro, trifluoromethyl or methoxy; and W is oxy.

A group of compounds which is preferred among the R Group of compounds, designated the Z Group, contains those compounds wherein Q is —($C_2$–$C_4$)alkylene-W—X—W—($C_1$–$C_3$)alkylene-;

W is oxy; and

X is thienyl or phenyl; said phenyl and thienyl optionally mono- or di-substituted independently with fluoro, chloro, trifluoromethyl or methoxy.

A group of compounds which is preferred among the R Group of compounds, designated the A1 Group, contains those compounds wherein
Q is —($C_1$–$C_4$)alkylene-ethenylene-($C_1$–$C_4$)alkylene-; and
M is —Ar and —Ar is phenyl, thiazolyl, pyridyl or thienyl.

A group of compounds which is preferred among the R Group of compounds, designated the B1 Group, contains those compounds wherein
Q is —($C_1$–$C_4$)alkylene-ethenylene-($C_0$–$C_2$)alkylene-X—($C_0$–$C_3$)alkylene-; and
X is thienyl or phenyl; said phenyl and thienyl optionally mono- or di-substituted independently with fluoro, chloro, trifluoromethyl or methoxy.

A group of compounds which is preferred among the R Group of compounds, designated the C1 Group, contains those compounds wherein
Q is —($C_1$–$C_3$)alkylene-ethenylene-($C_0$–$C_2$)alkylene-X—W—($C_1$–$C_3$)alkylene-;
W is oxy; and
X is thienyl or phenyl; said phenyl and thienyl optionally mono- or di-substituted independently with fluoro, chloro, trifluoromethyl or methoxy.

A group of compounds which is preferred among the R Group of compounds, designated the D1 Group, contains those compounds wherein
Q is —($C_1$–$C_4$)alkylene-ethynylene-($C_1$–$C_4$)alkylene-.

A group of compounds which is preferred among the R Group of compounds, designated the E1 Group, contains those compounds wherein
Q is —($C_1$–$C_4$)alkylene-ethynylene-X—($C_0$–$C_3$)alkylene-; and
X is thienyl or phenyl; said phenyl and thienyl optionally mono- or di-substituted independently with fluoro, chloro, trifluoromethyl or methoxy.

A group of compounds which is preferred among the C Group of compounds, designated the F1 Group, contains those compounds wherein
A is ($C_1$–$C_3$)alkylsulfonyl;
K is oxy($C_1$–$C_4$)alkylene;
—Ar is phenyl, thienyl, thiazolyl, pyridyl, benzo[1,3]dioxolyl, cyclopentyl or cyclohexyl; and
$R^1$, $R^2$ and R are each independently hydroxy, halo, trifluoromethyl, difluoromethoxy, trifluoromethoxy, ($C_1$–$C_4$)alkoxy or ($C_1$–$C_7$)alkyl.

Especially preferred compounds within the F1 Group are
7-{[2-(3,5-Dichloro-phenoxy)-ethyl]-methanesulfonyl-amino}heptanoic acid,
5-(3-{[2-(3,5-Dichloro-phenoxy)-ethyl]-methanesulfonyl-amino}-propyl)-thiophene-2-carboxylic acid and
N-[2-(3,5-Dichloro-phenoxy)-ethyl]-N-[6-(1 H-tetrazol-5-yl)-hexyl]-methanesulfonamide.

A group of compounds which is preferred among the F1 Group of compounds, designated the G1 group, contains those compounds wherein
Q is —($C_2$–$C_6$)alkylene-W—($C_1$–$C_3$)alkylene-; and
W is oxy.

A group of compounds which is preferred among the F1 Group of compounds, designated the H1 Group, contains those compounds wherein
Q is —($C_3$–$C_8$)alkylene-, said —($C_3$–$C_8$)alkylene- optionally substituted with from one to four fluorines.

An especially preferred compound among the H1 group of compounds is a compound wherein A is methylsulfonyl;
Q is n-hexylene;
Z is carboxyl;
K is oxyethylene; and
M is 3,5-dichlorophenyl.

A group of compounds which is preferred among the F1 Group of compounds, designated the 11 Group, contains those compounds wherein
Q is —X—($C_1$–$C_5$)alkylene-; and
X is thienyl or phenyl; said phenyl and thienyl optionally mono- or di-substituted independently with fluoro, chloro, trifluoromethyl or methoxy.

A group of compounds which is preferred among the F1 Group of compounds, designated the J1 Group, contains those compounds wherein
Q is —($C_1$–$C_5$)alkylene-X—; and
X is thienyl or phenyl; said phenyl and thienyl optionally mono- or di-substituted independently with fluoro, chloro, trifluoromethyl or methoxy.

An especially preferred compound among the J1 group is a compound wherein
A is methylsulfonyl;
Q—Z is 3-(2-carboxylthien-5-yl)-n-propylene;
K is oxyethylene; and
M is 3,5-dichlorophenyl.

A group of compounds which is preferred among the F1 Group of compounds, designated the K1 Group, contains those compounds wherein
Q is —($C_1$–$C_3$)alkylene-X—($C_1$–$C_3$)alkylene-; and
X is thienyl or phenyl; said phenyl and thienyl optionally mono- or di-substituted independently with fluoro, chloro, trifluoromethyl or methoxy.

A group of compounds which is preferred among the F1 Group of compounds, designated the L1 Group, contains those compounds wherein
Q is —($C_2$–$C_4$)alkylene-W—X—($C_0$–$C_3$)alkylene-;
X is thienyl or phenyl; said phenyl and thienyl optionally mono- or di-substituted independently with fluoro, chloro, trifluoromethyl or methoxy; and
W is oxy.

A group of compounds which is preferred among the F1 Group of compounds, designated the M1 Group, contains those compounds wherein
Q is —($C_0$–$C_4$)alkylene-X—W—($C_1$–$C_3$)alkylene-;
X is thienyl or phenyl; said phenyl and thienyl optionally mono- or di-substituted independently with fluoro, chloro, trifluoromethyl or methoxy; and
W is oxy.

A group of compounds which is preferred among the F1 Group of compounds, designated the N1 Group, contains those compounds wherein
Q is —($C_2$–$C_4$)alkylene-W—X—W—($C_1$–$C_3$)alkylene-;
W is oxy; and
X is thienyl or phenyl; said phenyl and thienyl optionally mono- or di-substituted independently with fluoro, chloro, trifluoromethyl or methoxy.

A group of compounds which is preferred among the F1 Group of compounds, designated the O1 Group, contains those compounds wherein
Q is —($C_1$–$C_4$)alkylene-ethenylene-($C_1$–$C_4$)alkylene-; and
M is —Ar and —Ar is phenyl, thiazolyl, pyridyl or thienyl.

A group of compounds which is preferred among the F1 Group of compounds, designated the P1 Group, contains those compounds wherein Q is —$(C_1-C_4)$alkylene-ethenylene-$(C_0-C_2)$alkylene-X—$(C_0-C_3)$alkylene-; and X is thienyl or phenyl; said phenyl and thienyl optionally mono- or di-substituted independently with fluoro, chloro, trifluoromethyl or methoxy.

A group of compounds which is preferred among the F1 Group of compounds, designated the Q1 Group, contains those compounds wherein Q is —$(C_1-C_3)$alkylene-ethenylene-$(C_0-C_2)$alkylene-X—W—$(C_1-C_3)$alkylene-;

W is oxy; and

X is thienyl or phenyl; said phenyl and thienyl optionally mono- or di-substituted independently with fluoro, chloro, trifluoromethyl or methoxy.

A group of compounds which is preferred among the F1 Group of compounds, designated the R1 Group, contains those compounds wherein Q is —$(C_1-C_4)$alkylene-ethynylene-$(C_1-C_4)$alkylene-.

A group of compounds which is preferred among the F1 Group of compounds, designated the S1 Group, contains those compounds wherein Q is —$(C_1-C_4)$alkylene-ethynylene-X—$(C_0-C_3)$alkylene-; and X is thienyl or phenyl; said phenyl and thienyl optionally mono- or di-substituted independently with fluoro, chloro, trifluoromethyl or methoxy.

A group of compounds which is preferred among the C1 Group of compounds, designated the T1 Group, contains those compounds wherein A is $(C_1-C_3)$alkylsulfonyl;

K is $(C_3-C_8)$alkylene, said $(C_3-C_8)$alkylene being mono-unsaturated;

—Ar is phenyl, thienyl, thiazolyl, pyridyl, cyclopentyl or cyclohexyl; and $R^1$, $R^2$ and $R^3$ are each independently hydroxy, halo, trifluoromethyl, difluoromethoxy, trifluoromethoxy, $(C_1-C_4)$alkoxy or $(C_1-C_7)$alkyl.

Especially preferred compounds among the T1 Group are

Trans-(4-{[3-(3,5-Dichloro-phenyl)-allyl]-methanesulfonyl-amino}-butoxy)-acetic acid, Trans-N-[3-(3,5-Dichloro-phenyl)-allyl]-N-[6-(1H-tetrazolyl-5-yl)-hexyl]-methanesulfonamide, Trans-5-(3-{[3-(3,5-Dichloro-phenyl)-allyl]-methanesulfonyl-amino}-propyl)-thiophene-2-carboxylic acid and Trans-[3-({[3-(3,5-Dichloro-phenyl)-allyl]-methanesulfonyl-amino}-methyl)-phenyl]-acetic acid.

A group of compounds which is preferred among the T1 Group of compounds, designated the U1 Group, contains those compounds wherein Q is —$(C_2-C_6)$alkylene-W—$(C_1-C_3)$alkylene-; and W is oxy.

An especially preferred compound among the U1 group is a compound wherein

A is methylsulfonyl;

Q is methyloxy-n-butylene;

Z is carboxyl;

K is trans-2-n-propeneylene; and

M is 3,5-dichlorophenyl.

A group of compounds which is preferred among the T1 Group of compounds, designated the V1 Group, contains those compounds wherein Q is —$(C_3-C_8)$alkylene-, said —$(C_3-C_8)$alkylene-optionally substituted with from one to four fluorines.

A preferred compound among the V1 group of compound is a compound herein

A is methylsulfonyl;

Q is n-hexylene;

Z is 5-(1H-tetrazolyl);

K is trans-2-n-propeneylene; and

M is 3,5-dichlorophenyl.

A group of compounds which is preferred among the T1 Group of compounds, designated the W1 Group, contains those compounds wherein Q is —X—$(C_1-C_5)$alkylene-; and X is thienyl or phenyl; said phenyl and thienyl optionally mono- or di-substituted independently with fluoro, chloro, trifluoromethyl or methoxy.

A group of compounds which is preferred among the T1 Group of compounds, designated the X1 Group, contains those compounds wherein Q is —$(C_1-C_5)$alkylene-X—; and X is thienyl or phenyl; said phenyl and thienyl optionally mono- or di-substituted independently with fluoro, chloro, trifluoromethyl or methoxy.

A preferred compound among the X1 Group is a compound wherein

A is methylsulfonyl;

Q—Z is 3-(2-carboxylthien-5-yl)-n-propylene;

K is trans-2-n-propeneylene; and

M is 3,5-dichlorophenyl.

A group of compounds which is preferred among the T1 Group of compounds, designated the Y1 Group, contains those compounds wherein Q is -$(C_1-C_3)$alkylene-X—$(C_1-C_3)$alkylene-; and X is thienyl or phenyl; said phenyl and thienyl optionally mono- or di-substituted independently with fluoro, chloro, trifluoromethyl or methoxy.

A group of compounds which is preferred among the T1 Group of compounds, designated the Z1 Group, contains those compounds wherein Q is —$(C_2-C_4)$alkylene-W—X—$(C_0-C_3)$alkylene-;

X is thienyl or phenyl; said phenyl and thienyl optionally mono- or di-substituted independently with fluoro, chloro, trifluoromethyl or methoxy; and W is oxy.

A group of compounds which is preferred among the T1 Group of compounds, designated the A2 Group, contains those compounds wherein Q is —$(C_0-C_4)$alkylene-X—W—$(C_1-C_3)$alkylene-;

X is thienyl or phenyl; said phenyl and thienyl optionally mono- or di-substituted independently with fluoro, chloro, trifluoromethyl or methoxy; and W is oxy.

A group of compounds which is preferred among the T1 Group of compounds, designated the B2 Group, contains those compounds wherein Q is —$(C_2-C_4)$alkylene-W—X—W—$(C_1-C_3)$alkylene-;

W is oxy; and

X is thienyl or phenyl; said phenyl and thienyl optionally mono- or di-substituted independently with fluoro, chloro, trifluoromethyl or methoxy.

A group of compounds which is preferred among the T1 Group of compounds, designated the C2 Group, contains those compounds wherein Q is —($C_1$–$C_4$)alkylene-ethenylene-($C_1$–$C_4$)alkylene-; and M is —Ar and —Ar is phenyl, thiazolyl, pyridyl or thienyl.

A group of compounds which is preferred among the T1 Group of compounds, designated the D2 Group, contains those compounds wherein Q is —($C_1$–$C_4$)alkylene-ethenylene-($C_0$–$C_2$)alkylene-X—($C_0$–$C_3$)alkylene-; and X is thienyl or phenyl; said phenyl and thienyl optionally mono- or di-substituted independently with fluoro, chloro, trifluoromethyl or methoxy.

A group of compounds which is preferred among the T1 Group of compounds, designated the E2 Group, contains those compounds wherein Q is —($C_1$–$C_3$)alkylene-ethenylene-($C_0$–$C_2$)alkylene-X—W—($C_1$–$C_3$)alkylene-;

W is oxy; and

X is thienyl or phenyl; said phenyl and thienyl optionally mono- or di-substituted independently with fluoro, chloro, trifluoromethyl or methoxy.

A group of compounds which is preferred among the T1 Group of compounds, designated the F2 Group, contains those compounds wherein Q is —($C_1$–$C_4$)alkylene-ethynylene-($C_1$–$C_4$)alkylene-.

A group of compounds which is preferred among the T1 Group of compounds, designated the G2 Group, contains those compounds wherein Q is —($C_1$–$C_4$)alkylene-ethynylene-X—($C_0$–$C_3$)alkylene-; and X is thienyl or phenyl; said phenyl and thienyl optionally mono- or di-substituted independently with fluoro, chloro, trifluoromethyl or methoxy.

A preferred group of compounds, designated the H2 Group, contains those compounds having the Formula I as shown above wherein B is N;

A is ($C_1$–$C_6$)alkanoyl, or ($C_3$–$C_7$)cycloalkyl($C_1$–$C_6$)alkanoyl, said A moieties optionally mono-, di- or tri-substituted on carbon independently with hydroxy or halo;

X is phenyl, thienyl, or thiazolyl said phenyl, thienyl or thiazolyl optionally mono- or di-substituted independently with fluoro, chloro, trifluoromethyl, methoxy, difluoromethoxy or trifluoromethoxy;

W is oxy, thio or sulfonyl;

Z is carboxyl, ($C_1$–$C_4$)alkoxycarbonyl or tetrazolyl;

K is ($C_1$–$C_8$)alkylene or oxy($C_1$–$C_4$)alkylene, said ($C_1$–$C_8$)alkylene optionally mono-unsaturated and wherein K is optionally mono-, di- or tri-substituted independently with methyl, fluoro or chloro;

Ar is ($C_5$–$C_7$)cycloalkyl, phenyl, thienyl, pyridyl, thiazolyl, oxazolyl, isoxazolyl, naphthalenyl, benzo[b]furanyl, benzo[b]thiophenyl, indanyl, furanyl, benzo[1,3]dioxolyl, benzimidazolyl, benzisoxazolyl, 2,3-dihydrobenzo[1,4]dioxinyl, 2,3-dihydrobenzofuranyl, pyrazolyl, pyrimidyl, pyrazinyl, imidazolyl, quinolinyl, isoquinolinyl, benzoxazolyl, benzothiazolyl, indolyl, 1,2,3,4-tetrahydronaphthalenyl, cyclohexyl, cyclopentyl, or chromanyl;

$Ar^1$ and $Ar^2$ are each independently ($C_5$–$C_7$)cycloalkyl, phenyl, thienyl, thiazolyl, pyridyl, pyrimidyl, oxazolyl, furanyl, imidazolyl, isoxazolyl, pyrazinyl or pyrazolyl;

$R^1$ is halo, ($C_0$–$C_6$)alkoxy, ($C_1$–$C_7$)alkyl, ($C_3$–$C_7$)cycloalkyl, ($C_1$–$C_7$)alkanoyl or ($C_3$–$C_7$)cycloalkyl($C_1$–$C_4$)alkyl, said ($C_1$–$C_6$)alkoxy, ($C_1$–$C_7$)alkyl, ($C_3$–$C_7$)cycloalkyl, ($_1$–$C_7$)alkanoyl or ($C_3$–$C_7$)cycloalkyl($C_1$–$C_4$)alkyl, optionally mono-, di- or tri-substituted independently with hydroxy, fluoro or chloro; and $R^2$ and $R^3$ are each independently hydroxy, halo, difluoromethoxy, trifluoromethoxy, trifluoromethyl, ($C_1$–$C_7$)alkyl, ($C_1$–$C_4$)alkoxy, ($C_1$–$C_5$)alkanoyl, cyano, ($C_3$–$C_7$)cycloalkyl, ($C_3$–$C_7$)cycloalkyl($C_1$–$C_4$)alkyl, formyl or carbamoyl.

It is especially preferred for the H2 Group that K is not optionally mono-, di- or tri-substituted independently with methyl, fluoro or chloro.

A group of compounds which is preferred among the H2 Group of compounds, designated the 12 Group, contains those compounds wherein A is ($C_1$–$C_6$)alkanoyl, said ($C_1$–$C_6$)alkanoyl optionally mono-, di- or tri-substituted on carbon independently with halo;

Q is

—($C_2$–$C_6$)alkylene-W—($C_1$–$C_3$)alkylene-,

—($C_4$–$C_8$)alkylene-, said —($C_4$–$C_8$)alkylene- optionally substituted with up to four substituents independently selected from fluoro or ($C_1$–$C_4$)alkyl, —X—($C_2$–$C_5$)alkylene-, —($C_1$–$C_5$)alkylene-X—, —($C_1$–$C_3$)alkylene-X—($C_1$–$C_3$)alkylene-, —($C_2$–$C_4$)alkylene-W—X—($C_0$–$C_3$)alkylene-, or —($C_0$–$C_4$)alkylene-X—W—($C_1$–$C_3$)alkylene-, K is methylene or ethylene;

M is —$Ar^1$—V—$Ar^2$ or —$Ar^1$—O—$Ar^2$ wherein $Ar^1$ and $Ar^2$ are each independently phenyl, pyridyl or thienyl;

V is a bond or ($C_1$–$C_2$)alkylene;

$R^1$ is chloro, fluoro, ($C_1$–$C_4$)alkyl or ($C_1$–$C_6$)alkoxy, said ($C_1$–$C_4$)alkyl) and ($C_1$–$C_6$)alkoxy optionally mono-, di-or tri-substituted independently with hydroxy or fluoro; and $R^2$ and $R^3$ are each independently chloro or fluoro.

A group of compounds which is preferred among the H2 Group of compounds, designated the J2 Group, contains those compounds wherein A is ($C_1$–$C_6$)alkanoyl said ($C_1$–$C_6$)alkanoyl optionally mono-, di- or tri-substituted independently on carbon with hydroxy or halo;

K is methylene;

Q is

—($C_2$–$C_6$)alkylene-W—($C_1$–$C_3$)alkylene-,

—($C_4$–$C_8$)alkylene-, said —($C_4$–$C_8$)alkylene- optionally substituted with up to four substituents independently selected from fluoro or ($C_1$–$C_4$)alkyl, —X—($C_2$–$C_5$)alkylene-, —($C_1$–$C_5$)alkylene-X—, —($C_1$–$C_3$)alkylene-X—($C_1$–$C_3$)alkylene-, —($C_2$–$C_4$)alkylene-W—X—($C_0$–$C_3$)alkylene-, or —($C_0$–$C_4$)alkylene-X—W—($C_1$–$C_3$)alkylene-;

M is —Ar and —Ar is phenyl, thiazolyl, pyridyl, thienyl, oxazolyl, furanyl, cyclopentyl or cyclohexyl wherein —Ar is substituted with at least $R^1$;

$R^1$ is ($C_1$–$C_7$)alkyl or ($C_1$–$C_5$)alkoxy, said ($C_{1–C7}$)alkyl or ($C_1$–$C_5$)alkoxy optionally mono-, di- or tri-substituted independently with hydroxy or fluoro; and $R^2$ and $R^3$ are each independently chloro, fluoro, methyl, difluoromethoxy, trifluoromethoxy or trifluoromethyl.

A group of compounds which is preferred among the H2 Group of compounds, designated the K2 Group, contains those compounds wherein A is $(C_1-C_6)$alkanoyl, said $(C_1-C_6)$alkanoyl optionally mono-, di- or tri-substituted on carbon independently with halo;

K is $(C_1-C_8)$alkylene;

Q is

—$(C_2-C_6)$alkylene-W—$(C_1-C_3)$alkylene-,

—$(C_4-C_8)$alkylene-, said -$(C_4-C_8)$alkylene- optionally substituted with up to four substituents independently selected from fluoro or $(C_1-C_4)$alkyl, —X—$(C_2-C_5)$alkylene-, —$(C_1-C_5)$alkylene-X—, —$(C_1-C_3)$alkylene-X—$(C_1-C_3)$alkylene-, —$(C_2-C_4)$alkylene-W—X—$(C_0-C_3)$alkylene-, or —$(C_0-C_4)$alkylene-X—W—$(C_1-C_3)$alkylene-;

M is —Ar and —Ar is phenyl, thienyl, benzofuranyl, benzo[1,3]dioxolyl, 2,3—dihydrobenzo[1,4]dioxinyl, 2,3-dihydrobenzofuranyl, benzimidazolyl, benzo[b]thiophenyl, cyclopentyl or cyclohexyl; and $R^1$, $R^2$ and $R^3$ are each independently hydroxy, halo, trifluoromethyl, difluoromethoxy, trifluoromethoxy, $(C_1-C_4)$alkoxy or $(C_1-C_7)$alkyl.

A group of compounds which is preferred among the H2 Group of compounds, designated the L2 Group, contains those compounds wherein A is $(C_1-C_6)$alkanoyl, said $(C_1-C_6)$alkanoyl optionally mono-, di- or tri-substituted on carbon independently with halo;

K is oxy$(C_1-C_4)$alkylene;

Q is

—$(C_2-C_6)$alkylene-W—$(C_1-C_3)$alkylene-,

—$(C_4-C_8)$alkylene-, said —$(C_4-C_8)$alkylene- optionally substituted with up to four substituents independently selected from fluoro or $(C_1-C_4)$alkyl, —X—$(C_2-C_5)$alkylene-, —$(C_1-C_5)$alkylene-X—, —$(C_1-C_3)$alkylene-X—$(C_1-C_3)$alkylene-, —$(C_2-C_4)$alkylene-W—X—$(C_0-C_3)$alkylene-, or —$(C_0-C_4)$alkylene-X—W—$(C_1-C_3)$alkylene-;

M is —Ar and —Ar is phenyl, thienyl, benzo[1,3]dioxolyl, cyclopentyl or cyclohexyl; and $R^1$, $R^2$ and $R^3$ are each independently hydroxy, halo, trifluoromethyl, difluoromethoxy, trifluoromethoxy, $(C_1-C_4)$alkoxy or $(C_1-C_7)$alkyl.

A group of compounds which is preferred among the H2 Group of compounds, designated the M2 Group, contains those compounds wherein A is $(C_3-C_6)$alkanoyl said $(C_3-C_6)$alkanoyl optionally mono-, di- or tri-substituted on carbon independently with halo;

K is $(C_3-C_8)$alkylene, said $(C_3-C_8)$alkylene being mono-unsaturated;

Q is

—$(C_2-C_6)$alkylene-W—$(C_1-C_3)$alkylene-,

—$(C_4-C_8)$alkylene-, said —$(C_4-C_8)$alkylene- optionally substituted with up to four substituents independently selected from fluoro or $(C_1-C_4)$alkyl, —X—$(C_2-C_5)$alkylene-, —$(C_1-C_5)$alkylene-X—, —$(C_1-C_3)$alkylene-X—$(C_1-C_3)$alkylene-, —$(C_2-C_4)$alkylene-W—X—$(C_0-C_3)$alkylene-, or —$(C_0-C_4)$alkylene-X—W—$(C_1-C_3)$alkylene-;

M is —Ar and —Ar is phenyl, thienyl, cyclopentyl or cyclohexyl; and $R^1$, $R^2$ and $R^3$ are each independently hydroxy, halo, trifluoromethyl, trifluoromethoxy, $(C_1-C_4)$alkoxy or $(C_1-C_7)$alkyl.

A preferred group of compounds, designated the N2 Group, contains those compounds having the Formula I as shown above wherein B is C(H);

A is $(C_1-C_6)$alkanoyl, or $(C_3-C_7)$cycloalkyl$(C_1-C_6)$alkanoyl, said A moieties optionally mono-, di- or tri-substituted on carbon independently with hydroxy or halo;

X is phenyl, thienyl, or thiazolyl said phenyl, thienyl or thiazolyl optionally mono- or di-substituted independently with fluoro, chloro, trifluoromethyl, methoxy, difluoromethoxy or trifluoromethoxy;

W is oxy, thio or sulfonyl;

Z is carboxyl, $(C_1-C_4)$alkoxycarbonyl or tetrazolyl;

K is $(C_1-C_8)$alkylene or oxy$(C_1-C_4)$alkylene, said $(C_1-C_8)$alkylene optionally mono-unsaturated and wherein K is optionally mono-, di- or tri-substituted independently with hydroxy, fluoro or chloro;

Ar is $(C_5-C_7)$cycloalkyl, phenyl, thienyl, pyridyl, thiazolyl, oxazolyl, isoxazolyl, naphthalenyl, benzo[b]furanyl, benzo[b]thiophenyl, indanyl, furanyl, benzo[1,3]dioxolyl, benzimidazolyl, benzisoxazolyl, 2,3-dihydrobenzo[1,4]dioxinyl, 2,3-dihydrobenzofuranyl, pyrazolyl, pyrimidyl, pyrazinyl, imidazolyl, quinolinyl, isoquinolinyl, benzoxazolyl, benzothiazolyl, indolyl, 1,2,3,4-tetrahydronaphthalenyl, cyclohexyl, cyclopentyl, or chromanyl;

$Ar^1$ and $Ar^2$ are each independently $(C_5-C_7)$cycloalkyl, phenyl, thienyl, thiazolyl, pyridyl, pyrimidyl, oxazolyl, furanyl, imidazolyl, isoxazolyl, pyrazinyl or pyrazolyl;

$R^1$ is halo, $(C_1-C_6)$alkoxy, $(C_1-C_7)$alkyl, $(C_3-C_7)$cycloalkyl, $(C_1-C_7)$alkanoyl or $(C_3-C_7)$cycloalkyl$(C_1-C_4)$alkyl, said $(C_1-C_6)$alkoxy, $(C_1-C_7)$alkyl, $(C_3-C_7)$cycloalkyl, $(C_1-C_7)$alkanoyl or $(C_3-C_7)$cycloalkyl$(C_1-C_4)$alkyl, optionally mono-, di- or tri-substituted independently with hydroxy, fluoro or chloro; and $R^2$ and $R^3$ are each independently hydroxy, halo, difluoromethoxy, trifluoromethoxy, trifluoromethyl, $(C_1-C_7)$alkyl, $(C_1-C_4)$alkoxy, $(C_1-C_5)$alkanoyl, cyano, $(C_3-C_7)$cycloalkyl, $(C_3-C_7)$cycloalkyl$(C_1-C_4)$alkyl, formyl or carbamoyl.

It is especially preferred for Group N2 that K is not optionally mono-, di- or tri-substituted independently with methyl, fluoro or chloro.

A group of compounds which is preferred among the N2 Group of compounds, designated the O2 Group, contains those compounds wherein A is $(C_1-C_6)$alkanoyl, said A optionally mono-, di- or tri-substituted on carbon independently with halo;

Q is

—$(C_2-C_6)$alkylene-W—$(C_1-C_3)$alkylene-,

—$(C_4-C_8)$alkylene-, said —$(C_4-C_8)$alkylene- optionally substituted with up to four substituents independently selected from fluoro or $(C_1-C_4)$alkyl, —X—$(C_2-C_5)$alkylene-, —($C_1$–$C_5$)alkylene-X—,
—($C_1$–$C_3$)alkylene-X—($C_1$–$C_3$)alkylene-,
—($C_2$–$C_4$)alkylene-W—X—($C_0$–$C_3$)alkylene-, or
—($C_0$–$C_4$)alkylene-X—W—($C_1$–$C_3$)alkylene-;
K is methylene or ethylene;
M is —$Ar^1$—V—$Ar^2$ or —$Ar^1$—O—$Ar^2$ wherein $Ar^1$ and $Ar^2$ are each independently phenyl, pyridyl or thienyl;
V is a bond or ($C_1$–$C_2$)alkylene;
$R^1$ is chloro, fluoro, ($C_1$–$C_4$)alkyl or ($C_1$–$C_4$)alkoxy, said ($C_1$–$C_4$)alkyl and ($C_1$–$C_4$)alkoxy optionally mono-, di- or tri-substituted independently with hydroxy or fluoro; and
$R^2$ and $R^3$ are each independently chloro or fluoro.

A group of compounds which is preferred among the N2 Group of compounds, designated the P2 Group, contains those compounds wherein
A is ($C_1$–$C_6$)alkanoyl, said A optionally mono-, di- or tri-substituted on carbon independently with hydroxy or halo;
K is methylene;
Q is
—($C_2$–$C_6$)alkylene-W—($C_1$–$C_3$)alkylene-,
($C_4$–$C_8$)alkylene-, said —($C_4$–$C_8$)alkylene- optionally substituted with up to four substituents independently selected from fluoro or ($C_1$–$C_4$)alkyl,
—X—($C_2$–$C_5$)alkylene-,
—($C_1$–$C_5$)alkylene-X—,
—($C_1$–$C_3$)alkylene-X—($C_1$–$C_3$)alkylene-,
—($C_2$–$C_4$)alkylene-W—X—($C_0$–$C_3$)alkylene-, or
—($C_0$–$C_4$)alkylene-X—W—($C_1$–$C_3$)alkylene-;
M is —Ar and —Ar is phenyl, thiazolyl, pyridyl, thienyl, oxazolyl, furanyl, cyclopentyl or cyclohexyl wherein —Ar is substituted with at least $R^1$;
$R^1$ is ($C_1$–$C_7$)alkyl or ($C_1$–$C_6$)alkoxy, said ($C_1$–$C_7$)alkyl or ($C_1$–$C_6$)alkoxy optionally mono-, di- or tri-substituted independently with hydroxy or fluoro; and
$R^2$ and $R^3$ are each independently chloro, fluoro, methyl, difluoromethoxy, trifluoromethoxy or trifluoromethyl.

A group of compounds which is preferred among the N2 Group of compounds, designated the Q2 Group, contains those compounds wherein
A is ($C_1$–$C_6$)alkanoyl, said A optionally mono-, di- or tri-substituted on carbon independently with halo;
K is ($C_1$–$C_8$)alkylene;
Q is
—($C_2$–$C_6$)alkylene-W—($C_1$–$C_3$)alkylene-,
—($C_4$–$C_8$)alkylene-, said —($C_4$–$C_8$)alkylene- optionally substituted with up to four substituents independently selected from fluoro or ($C_1$–$C_4$)alkyl,
—X—($C_2$–$C_5$)alkylene-,
—($C_1$–$C_5$)alkylene-X—,
—($C_1$–$C_3$)alkylene-X—($C_1$–$C_3$)alkylene-,
—($C_2$–$C_4$)alkylene-W—X—($C_0$–$C_3$)alkylene-, or
—($C_0$–$C_4$)alkylene-X—W—($C_1$–$C_3$)alkylene-;
M is —Ar and —Ar is phenyl, thienyl, benzofuranyl, benzo[1,3]dioxolyl, 2,3-dihydrobenzo[1,4]dioxinyl, 2,3-dihydrobenzofuranyl, benzimidazolyl, benzo[b]thiophenyl, cyclopentyl or cyclohexyl; and
$R^1$, $R^2$ and $R^3$ are each independently hydroxy, halo, trifluoromethyl, trifluoromethoxy, ($C_1$–$C_4$)alkoxy or ($C_1$–$C_7$)alkyl.

A group of compounds which is preferred among the N2 Group of compounds, designated the R2 Group, contains those compounds wherein
A is ($C_1$–$C_6$)alkanoyl said A optionally mono-, di- or tri-substituted on carbon independently with halo;
K is oxy($C_1$–$C_4$)alkylene;
Q is
—($C_2$–$C_6$)alkylene-W—($C_1$–$C_3$)alkylene-,
—($C_4$–$C_8$)alkylene-, said —($C_4$–$C_8$)alkylene- optionally substituted with up to four substituents independently selected from fluoro or ($C_1$–$C_4$)alkyl,
—X—($C_2$–$C_5$)alkylene-,
—($C_1$–$C_5$)alkylene-X—,
—($C_1$–$C_3$)alkylene-X—($C_1$–$C_3$)alkylene-,
—($C_2$–$C_4$)alkylene-W—X—($C_0$–$C_3$)alkylene-, or
—($C_0$–$C_4$)alkylene-X—W—($C_1$–$C_3$)alkylene-;
M is —Ar and —Ar is phenyl, thienyl, benzo[1,3]dioxolyl, cyclopentyl or cyclohexyl; and
$R^1$, $R^2$ and $R^3$ are each independently hydroxy, halo, trifluoromethyl, trifluoromethoxy, ($C_1$–$C_4$)alkoxy or ($C_1$–$C_7$)alkyl.

A group of compounds which is preferred among the N2 Group of compounds, designated the S2 Group, contains those compounds wherein
A is ($C_1$–$C_6$)alkanoyl, said A optionally mono-, di- or tri-substituted on carbon independently with halo;
K is ($C_3$–$C_8$)alkylene, said ($C_3$–$C_8$)alkylene being mono-unsaturated;
Q is
—($C_2$–$C_6$)alkylene-W—($C_1$–$C_3$)alkylene-,
—($C_4$–$C_8$)alkylene-, said —($C_4$–$C_8$)alkylene- optionally substituted with up to four substituents independently selected from fluoro or ($C_1$–$C_4$)alkyl,
—X—($C_2$–$C_5$)alkylene-,
—($C_1$–$C_5$)alkylene-X—,
—($C_1$–$C_3$)alkylene-X—($C_1$–$C_3$)alkylene-,
—($C_2$–$C_4$)alkylene-W—X—($C_0$–$C_3$)alkylene-, or
—($C_0$–$C_4$)alkylene-X—W—($C_1$–$C_3$)alkylene-;
M is —Ar and —Ar is phenyl, thienyl, cyclopentyl or cyclohexyl; and
$R^1$, $R^2$ and $R^3$ are each independently hydroxy, halo, trifluoromethyl, trifluoromethoxy, ($C_1$–$C_4$)alkoxy or ($C_1$–$C_7$)alkyl.

An especially preferred compound of the J2 Group of compounds is a compound wherein
A is propanoyl;
Q is n-hexylene;
Z is carboxyl;
K is methylene; and
M is 4-(n-1-hydroxylhexyl)phenyl.

An especially preferred compound among the H1 Group of compounds is a compound wherein
A is methylsulfonyl;
Q is n-hexylene;
Z is 5-(1H-tetrazolyl);
K is oxyethyl; and
M is 3,5-dichlorophenyl.

An especially preferred compound among the Y1 Group of compounds is a compound wherein
A is methylsulfonyl;
Q is 3-methylenephenylmethyl;

Z is carboxyl;

K is trans-2-n-propenylene; and

M is 3,5-dichlorophenyl.

An especially preferred group of compounds is (3-{[(4-Butyl-benzyl)-methanesulfonyl-amino]-methyl}-phenyl)-acetic acid;

7-{[4-(1-Hydroxy-hexyl)-benzyl]-methanesulfonyl-amino}-heptanoic acid;

7-[(4-Hydroxy-nonyl)-methanesulfonyl-amino]-heptanoic acid;

7-[(2'-Hydroxymethyl-biphenyl-4-ylmethyl)-methanesulfonyl-amino]-heptanoic acid;

7-[(4-Butyl-benzyl)-methanesulfonyl-amino]-heptanoic acid;

7-{[2-(3,5-Dichloro-phenoxy)-ethyl]-methanesulfonyl-amino}-heptanoic acid;

5-(3-{[3-(3-Chloro-phenyl)-propyl]-methanesulfonyl-amino}-propyl)-thiophene-2-carboxylic acid;

Trans-[3-({[3-(3,5-Dichloro-phenyl)-allyl]-methanesulfonyl-amino}-methyl)-phenyl]-acetic acid; or N-[2-(3,5-Dichloro-phenoxy)-ethyl]-N-[6-(1H-tetrazol-5-yl)-hexyl]-methanesulfonamide.

A preferred dosage is about 0.001 to 100 mg/kg/day of the Formula I compound. An especially preferred dosage is about 0.01 to 50 mg/kg/day of the Formula I compound.

By selectively agonizing the EP2 receptor subtype is meant selectively binding to the EP2 receptor subtype preferentially (by at least 5 fold) over the EP1, EP3 and EP4 and interacting with the EP2 receptor resulting in increased cyclic AMP production.

By selective EP2 agonist is meant a compound that binds to the EP2 receptor preferentially (by at least 5 fold) over the EP1, EP3, EP4. In addition, a selective EP2 agonist binds and interacts with the EP2 receptor resulting in increased cyclic AMP production.

The phrase "condition(s) which presents with low bone mass" refers to a condition where the level of bone mass is below the age specific normal as defined in standards by the World Health Organization "Assessment of Fracture Risk and its Application to Screening for Postmenopausal Osteoporosis (1994). Report of a World Health Organization Study Group. World Health Organization Technical Series 843". Included in "condition(s) which presents with low bone mass" are primary and secondary osteoporosis. Secondary osteoporosis includes glucocorticoid-induced osteoporosis, hyperthyroidism-induced osteoporosis, immobilization-induced osteoporosis, heparin-induced osteoporosis and immunosuppressive-induced osteoporosis. Also included is periodontal disease, alveolar bone loss, osteotomy bone loss and childhood idiopathic bone loss. The "condition(s) which presents with low bone mass" also includes long term complications of osteoporosis such as curvature of the spine, loss of height, prosthetic surgery.

The phrase "condition which presents with low bone mass" also refers to a mammal known to have a significantly higher than average chance of developing such diseases as are described above including osteoporosis (e.g., post-menopausal women, men over the age of 60.

Other bone mass augmenting or enhancing uses include increasing the bone fracture healing rate, enhancing the rate of successful bone grafts, bone healing following facial reconstruction or maxillary reconstruction or mandibular reconstruction, prosthetic ingrowth, vertebral synostosis or long bone extension.

Those skilled in the art will recognize that the term bone mass actually refers to bone mass per unit area which is sometimes (although not strictly correctly) referred to as bone mineral density.

The term "treating", "treat" or "treatment" as used herein includes preventative (e.g., prophylactic) and palliative treatment.

By "pharmaceutically acceptable" it is meant the carrier, diluent, excipients, and/or salt must be compatible with the other ingredients of the formulation, and not deleterious to the recipient thereof.

The expression "prodrug" refers to compounds that are drug precursors, which following administration, release the drug in vivo via some chemical or physiological process (e.g., a prodrug on being brought to the physiological pH is converted to the desired drug form). Exemplary prodrugs upon cleavage release the corresponding free acid, and such hydrolyzable ester-forming residues of the Formula I compounds include but are not limited to substituents wherein the Z moiety is independently carboxyl and the free hydrogen is replaced by $(C_1-C_4)$alkyl, $(C_2-C_7)$alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton4-yl, di-N,N—$(C_1-C_2)$alkylamino$(C_2-C_3)$alkyl (such as b-dimethylaminoethyl), carbamoyl-$(C_1-C_2)$alkyl, N,N-di$(C_1-C_2)$alkylcarbamoyl-$(C_1-C_2)$alkyl and piperidino-, pyrrolidino- or morpholino$(C_2-C_3)$alkyl.

By alkylene is meant saturated hydrocarbon (straight chain or branched) wherein a hydrogen atom is removed from each of the terminal carbons (e.g., methylene, ethylene, propylene, butylene, pentylene, hexylene, heptylene).

By halo is meant chloro, bromo, iodo, or fluoro.

By alkyl is meant straight chain saturated hydrocarbon or branched saturated hydrocarbon. Exemplary of such alkyl groups (assuming the designated length encompasses the particular example) are methyl, ethyl, propyl, isopropyl, butyl, sec-butyl, tertiary butyl, pentyl, isopentyl, neopentyl, tertiary pentyl, 1-methylbutyl, 2-methylbutyl, 3-methylbutyl, hexyl, isohexyl, heptyl and octyl.

By alkoxy is meant straight chain saturated alkyl or branched saturated alkyl bonded through an oxy. Exemplary of such alkoxy groups (assuming the designated length encompasses the particular example) are methoxy, ethoxy, propoxy, isopropoxy, butoxy, isobutoxy, tertiary butoxy, pentoxy, isopentoxy, neopentyl, tertiary pentyl, hexoxy, isohexoxy, heptoxy and octoxy.

As used herein the term mono-N- or di-N,N—$(C_1-C_x)$ alkyl . . . refers to the $(C_1-C_x)$alkyl moiety taken independently when it is di-N,N—$(C_1-C_x)$alkyl . . . (x refers to integers).

Unless otherwise stated the "M" moieties defined above are optionally substituted (e.g., the mere listing of a substituent such as $R^1$ in a subgenus or dependent claim does not mean that M is always substituted with the $R^1$ moiety unless it is stated that the M moiety is substituted with $R^1$.

It is to be understood that if a carbocyclic or heterocyclic moiety may be bonded or otherwise attached to a designated substrate, through differing ring atoms without denoting a specific point of attachment, then all possible points are intended, whether through a carbon atom or for example, a trivalent nitrogen atom. For example, the term "pyridyl" means 2-, 3-, or 4-pyridyl, the term "thienyl" means 2-, or 3-thienyl, and so forth.

The expression "pharmaceutically-acceptable salt" refers to nontoxic anionic salts containing anions such as (but not limited to) chloride, bromide, iodide, sulfate, bisulfate, phosphate, acetate, maleate, fumarate, oxalate, lactate, tartrate, citrate, gluconate, methanesulfonate and 4-toluene-sulfonate. The expression also refers to nontoxic cationic salts such as (but not limited to) sodium, potassium, calcium, magnesium, ammonium or protonated benzathine (N,N'- dibenzylethylenediamine), choline, ethanolamine, diethanolamine, ethylenediamine, meglamine (N-methylglucamine), benethamine (N-benzylphenethylamine), piperazine or tromethamine (2-amino-2-hydroxymethyl-1,3-propanediol).

As used herein, the expressions "reaction-inert solvent" and "inert solvent" refers to a solvent which does not interact with starting materials, reagents, intermediates or products in a manner which adversely affects the yield of the desired product.

The parenthetical negative or positive sign used herein in the nomenclature denotes the direction plane polarized light is rotated by the particular stereoisomer.

The chemist of ordinary skill will recognize that certain compounds of this invention will contain one or more atoms which may be in a particular stereochemical or geometric configuration, giving rise to stereoisomers and configurational isomers. All such isomers and mixtures thereof are included in this invention. Hydrates of the compounds of this invention are also included.

The chemist of ordinary skill will recognize that certain combinations of heteroatom-containing substituents listed in this invention define compounds which will be less stable under physiological conditions (e.g., those containing acetal or aminal linkages). Accordingly, such compounds are less preferred.

DTT means dithiothreitol. DMSO means dimethyl sulfoxide. EDTA means ethylenediamine tetraacetic acid.

The methods of this invention result in bone formation resulting in decreased fracture rates. This invention makes a significant contribution to the art by providing compounds and methods that increase bone formation resulting in prevention, retardation, and/or regression of osteoporosis and related bone disorders.

Other features and advantages will be apparent from the specification and claims which describe the invention.

DETAILED DESCRIPTION OF THE INVENTION

Any EP2 receptor subtype selective prostaglandin E2 agonist may be used as the active compound of this invention. The term selective EP2 agonist means a compound that binds to the EP2 receptor preferentially (by at least 5 fold) over the EP1, EP3, EP4. In addition, a selective EP2 agonist binds and interacts with the EP2 receptor resulting in increased cyclic AMP production (e.g., see the EP2 binding assay herein below and cyclic AMP assay herein below).

In general the EP2 selective compounds of this invention can be made by processes which include processes known in the chemical arts.

In particular, the Formula I compounds described above in the Summary may be prepared according to the following description.

Some substituents (e.g., carboxyl) may best be prepared through conversion of another functional group (for carboxyl examples are hydroxyl or carboxaldehyde) at a point later in the synthetic sequence.

In general, the Formula I compounds wherein B is nitrogen can be prepared by sequential alkylation of sulfonamide or amide with two appropriate alkyl halides or alkylsulfonates; or reductive amination of an amine containing the necessary acidic functionality (suitably protected) with an aldehyde followed by reaction with an acylating agent or a sulfonyl chloride followed by hydrolysis.

Generally, the compounds of Formula I (wherein B is N (nitrogen) and A, K, M and Q are as described in the Summary) can be prepared according to the methods described in SCHEMES 1 and 2 below. In general, the sequences involve sequential alkylation of the appropriate formula 1 sulfonamide or amide with two appropriate alkyl halides or alkylsulfonates. It is noted that SCHEMES 1 and 2 merely differ in the order of addition of the two alkylating agents. The alkylation order is typically chosen depending on the reactivity of the electrophilic side-chain. In order to reduce the amount of dialkylation which occurs in the first alkylation step, the less reactive electrophilic side-chain is typically introduced first. One of the alkylating agents typically contains a carboxylic acid or acid isostere suitably masked with an appropriate protecting group. In SCHEMES 1 and 2, the formula 3 acid precursor is a carboxylic ester where R represents either a straight chain lower alkyl, preferably methyl or ethyl, or a tert-butyl or phenyl group. Other acid isosteres can be employed by appropriately modifying these SCHEMES using methods known to those skilled in the art (see SCHEME 6 which describes a tetrazol preparation for an example). Typical alkylating agents are primary, secondary, benzylic or allylic and are preferably alkyl bromides or alkyl iodides.

The formula 1 sulfonamide or amide is converted to its anion with a strong base such as sodium hydride, lithium diisopropylamide, lithium bis(trimethylsilyl)amide, potassium bis(trimethylsilyl)amide, potassium tert-butoxide, etc. in an aprotic solvent such as dimethylformamide, tetrahydrofuran (THF) or dimethylformamide/benzene at a temperature of about −78° C. to about 100° C. The resulting anion is alkylated with the appropriate formula 2 or 3 alkyl halide or alkyl sulfonate (wherein X' is the halide or sulfonate) at a temperature of about 0° C. to about 100° C. to yield the corresponding alkylated formula 4 or 5 compound. In some cases, varying amounts of a side-product resulting from dialkylation of the amide or sulfonamide are obtained and can be removed using chromatographic techniques, preferably by flash chromatography (W. C. Still, M. Kahn, A. Mitra, J. Org. Chem. 43, 2923, 1978). The formula 4 or 5 compounds are converted to the anion again using a suitable base such as sodium hydride, lithium bis(trimethylsilyl)amide, lithium diisopropylamide, potassium bis(trimethylsilyl)amide, potassium tert-butoxide, or potassium carbonate in an aprotic solvent such as dimethylformamide, THF, dimethylformamide/benzene, or acetone at a temperature of about −78° C. to about 100° C. Alkylation (as described above) with the appropriate second alkyl halide or alkyl sulfonate (formula 3 or 2 compound) provides the corresponding formula 6 ester. The formula 6 ester is hydrolyzed to the corresponding Formula I acid (in cases where R represents methyl or ethyl) with a dilute aqueous basic solution (preferably sodium or potassium hydroxide in aqueous methanol or ethanol), lithium hydroxide in aqueous alcoholic solvent, aqueous tetrahydrofuran at a temperature of about 0° C. to about 80° C., or by using methods described in "Protecting Groups in Organic Synthesis," Second Edition, T. W. Greene and P. G. M. Wuts, John Wiley and Sons, Inc., 1991.

SCHEME 1

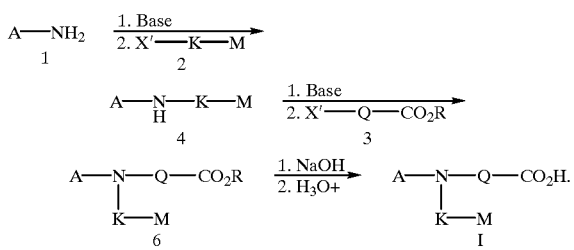

SCHEME 2

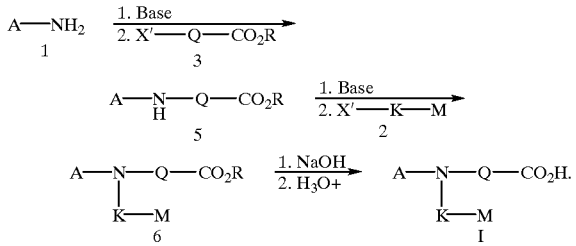

Formula I compounds (e.g., formula 13 or 14 compounds wherein B is N and A, K, M, Q and Z are as defined in the Summary) can also be prepared from amines (see SCHEMES 3–4 for examples). Generally, the appropriate amine starting materials (formula 9 and 10 compounds) can be commercially obtained or can be prepared using methods known to those skilled in the art (see "The Chemistry of Amino, Nitroso and Nitro Compounds and their Derivatives," Ed. S. Patai, J. Wiley, New York, 1982). For example, according to SCHEMES 3 and 4, the amine starting materials may be prepared from the corresponding formula 7 or 8 nitrites. Nitriles are either available from commercial sources or can be prepared using methods known to those skilled in the art (see Rappaport, "The Chemistry of the Cyano Group," interscience, New York, 1970 or Patai and Rappaport, "The Chemistry of Functional Groups," pt. 2, Wiley, N.Y., 1983). The formula 7 or 8 nitrile is reduced with a reducing agent such as borane-tetrahydrofuran complex, borane-methyl sulfide complex, lithium aluminum hydride, or hydrogenation in the presence of Raney nickel or a platinum or palladium catalyst in a protic solvent such as methanol or ethanol at a temperature of about 0° C. to about 50° C. The resulting formula 9 or 10 amine is converted to either the formula 11 or 12 sulfonamide or amide by treatment (acylation) with an acid chloride or sulfonyl chloride in the presence of a weak base such as triethylamine, pyridine, or 4-methylmorpholine in an aprotic solvent such as methylene chloride or diethyl ether at a temperature of about −20° C. to about 50° C. Alternatively, coupling of amines of formulas 9 or 10 with carboxylic acids are conveniently carried out in an inert solvent such as dichloromethane or N,N-dimethylformamide (DMF) by a coupling reagent such as 1-(3-dimethylaminopropyl)-3-ethylcarbodiimide hydrochloride (EDC) or 1,3-dicyclohexylcarbodiimide (DCC) in the presence of 1-hydroxybenzotriazole hydrate (HOBT) to generate compounds of formula 11 or 12. In the case where the amine is present as the hydrochloride salt, it is preferable to add one equivalent of a suitable base such as triethylamine to the reaction mixture. Alternatively, the coupling can be effected with a coupling reagent such as benzotriazol-1-yloxy-tris(dimethylamino)-phosphonium hexafluorophosphate (BOP) in an inert solvent such as methanol. Such coupling reactions are generally conducted at temperatures of about −30° C. to about 80° C., preferably 0° C. to about 25° C. For a discussion of other conditions used for coupling peptides see Houben-Weyl, Vol. XV, part II, E. Wunsch, Ed., George Theime Verlag, 1974, Stuttgart. Alkylation and if desired, deprotection, of the formula 11 or 12 compound as described in SCHEMES 1 and 2 affords the corresponding acid formula 13 and 14 compound.

The formula 9 and 10 amines may also be prepared via reduction of formula 15 and 16 amides. The reduction can be achieved using reagents such as a borane-tetrahydrofuran complex, a borane-methyl sulfide complex, or diisobutylaluminum hydride in an aprotic solvent such as tetrahydrofuran or diethyl ether at a temperature of about −78° C. to about 60° C.

The formula 9 and 10 amines can also be obtained from the corresponding nitro precursors by reduction of the nitro group using reducing reagents such as zinc/HCl, hydrogenation in the presence of Raney nickel, palladium, or platinum catalysts, and other reagents as described by P. N. Rylander in "Hydrogenation Methods," Academic Press, New York, 1985.

SCHEME 3

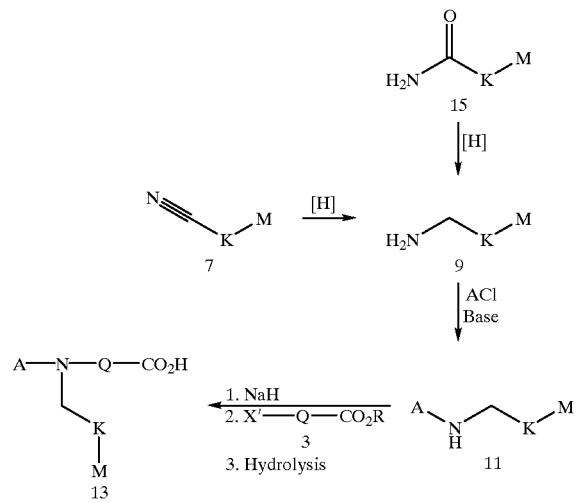

SCHEME 4

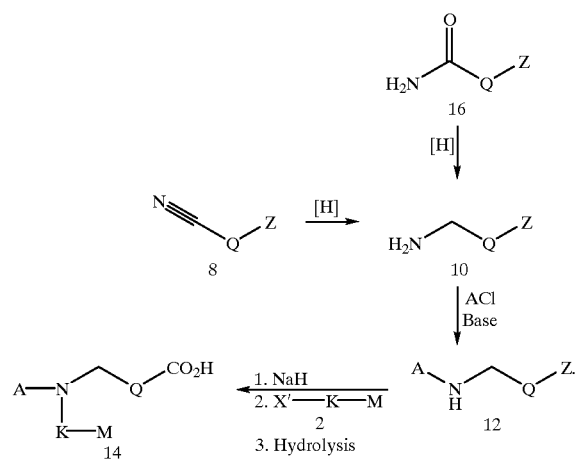

The description of, and preparation of other amines and alkylating agents useful for the above syntheses are described below in the section entitled PREPARATIONS.

An alternative to the alkylation chemistry described above for the preparation of Formula I compounds (wherein B is N and A, K, M and Q are as described in the Summary) involves reductive amination of an amine containing the necessary acidic functionality (suitably protected) with an aldehyde and is shown in SCHEME 5. Alternatively, the aldehyde may contain the acidic functionality for coupling with an amine.

The reductive amination is typically carried out with a reducing agent such as sodium cyanoborohydride or sodium triacetoxyborohydride preferably at a pH of between 6 and 8. The reaction is normally performed in a protic solvent such as methanol or ethanol at temperatures of about −78° C. to about 40° C. (for a leading reference see A. Abdel-Magid, C. Maryanoff, K. Carson, Tetrahedron Left. 39, 31, 5595–5598, 1990). Other conditions involve the use of titanium isopropoxide and sodium cyanoborohydride (R. J. Mattson et al, J. Org. Chem. 1990, 55, 2552–4) or preformation of the imine under dehydrating conditions followed by reduction. The resulting formula 42, 42A amine, is transformed to the desired sulfonamide or amide by coupling with an acid chloride, sulfonyl chloride, or carboxylic acid as described in SCHEMES 3 and 4. If desired, hydrolysis provides the corresponding acid.

SCHEME 5

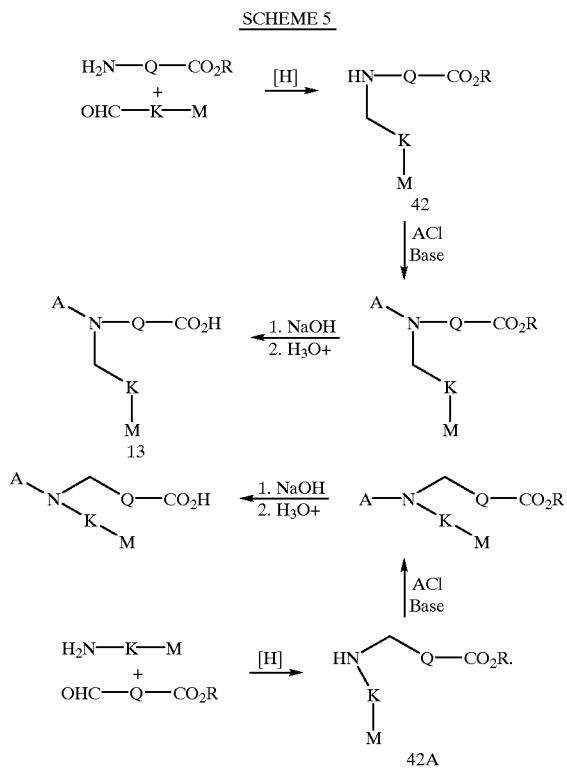

The description of and use of aldehydes useful in the above SCHEME 5 may be found in the PREPARATIONS section.

Alternatively, another method of preparing certain Formula I compounds (i.e., formula 60 tetrazoles wherein B is N and A, K, M, and Q are as described above) is described in SCHEME 6. The starting formula 4 sulfonamide or amide is alkylated with the appropriate alkyl halide or sulfonate (wherein X' is halide or sulfonate), preferable a primary, secondary, benzylic, or allylic alkyl bromide, iodide, or sulfonate, which contains a nitrile to provide formula 59 compounds. The alkylation is achieved by treatment of the formula 59 compound with a base such as sodium hydride, lithium bis(trimethylsilyl)amide, potassium bis(trimethylsilyl)amide, potassium tert-butoxide, or potassium carbonate in an aprotic solvent such as dimethylformamide, dimethylformamide/benzene, or acetone. Alkylation occurs at a temperature of about −78° C. to about 100° C. Preferred conditions for converting the resulting nitrile to the formula 60 tetrazole, involve treatment with dibutyltin oxide and trimethylsilylazide, in toluene at reflux (S. J. Wittenberger and B. G. Donner, J. Org. Chem. 1993, 58, 4139–4141, 1993). For a review of alternative preparations of tetrazoles see R. N. Butler, Tetrazoles, In Comprehensive Heterocyclic Chemistry; Potts, K. T. Ed.; Pergamon Press: Oxford, 1984, Vol. 5, pp 791–838.

SCHEME 6

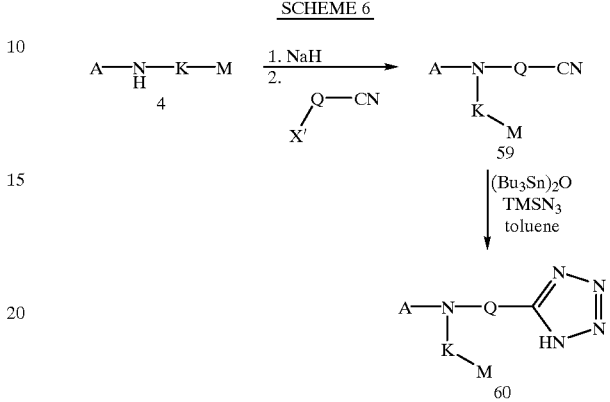

Alternatively, another method of preparing certain Formula I compounds (wherein B is N and A, Q and M are as described in the Summary) is described in SCHEME 7. Formula 46 esters can be prepared using the procedures described earlier (see SCHEMES 1 and 2). Subsequent Heck coupling of this intermediate to an arylhalide (preferably an aryl bromide or aryl iodide), an aryl triflate, or a ring system which contains a vinyl bromide, iodide, or triflate is accomplished with a palladium catalyst, such as palladium acetate or tetrakis(triphenylphosphine)palladium(0) in the presence of a trialkylamine, such as triethylamine. In some cases, a triarylphosphine may be added to the reaction. The reaction is typically performed in an aprotic solvent such as dimethylformamide or acetonitrile at a temperature of about 0° C. to about 150° C. (see R. F. Heck in Comp. Org. Syn., Vol. 4, Ch. 4.3, p. 833 or Daves and Hallberg, Chem. Rev. 1989, 89, 1433). If desired formula 47 compounds can be hydrolyzed to the corresponding acid. Alternatively, the formula 47 compounds can be hydrogenated and, if desired, further hydrolyzed to the corresponding formula 49 acid. Preferred conditions for hydrogenation involve the use of a palladium or platinum catalyst in an alcoholic solvent such as ethanol or methanol at a temperature of about 0° C. to about 50° C. In cases where M represents a partially saturated ring system, hydrogenation will generate a saturated ring system.

SCHEME 7

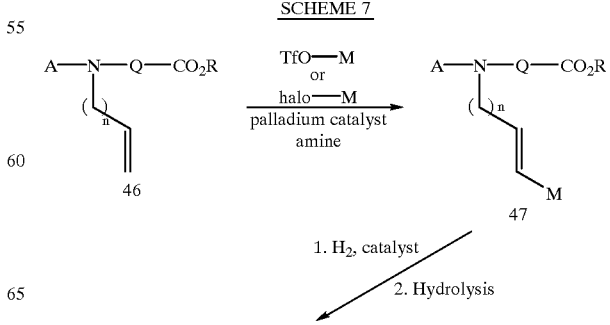

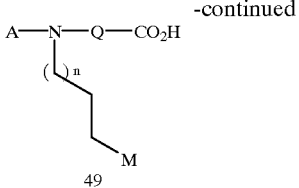

49

Alternatively, another method of preparing certain Formula I compounds (wherein B is N and A, Q, K and M are as described in the Summary and R is as described for SCHEMES 1 and 2) is described in SCHEME 8. Formula 51 compounds can be prepared as described in SCHEMES 1 and 2 by alkylation of formula 5 compounds with an electrophile of formula 2 which contains the appropriate functionality on the ring M, for subsequent conversion to an aldehyde. For example, electrophiles of formula 2 (SCHEME 2) could contain a protected alcohol on the ring, M, which, after alkylation, can be deprotected and oxidized to the aldehyde, using reagents known to those skilled in the art, to generate formula 51 compounds. An alternative method is to alkylate with an electrophile of formula 2 where M contains a vinyl group. After alkylation, oxidative cleavage of the double bond provides the desired formula 51 aldehyde. The oxidative cleavage can be accomplished by transforming the double bond to the 1,2-diol with catalytic osmium tetroxide and N-methylmorpholine followed by oxidative cleavage to the aldehyde using sodium periodate. Alternatively, oxidative cleavage via ozonolysis followed by reduction using reagents such as methyl sulfide, triphenylphosphine, zinc/acetic acid, or thiourea, will generate the desired formula 51 aldehyde. Addition of LMetal where LMetal represents any organometallic reagent such as an organolithium or Grignard reagent in an aprotic solvent such as diethyl ether or tetrahydrofuran at a temperature of about −78° C. to about 80° C., followed by hydrolysis of the ester as described above, provides the desired formula 50 compound.

SCHEME 8

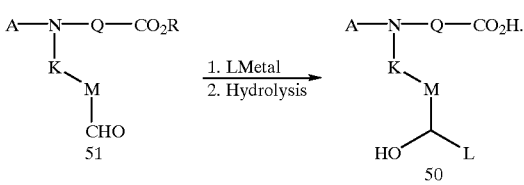

Alternatively, another method of preparing certain Formula I compounds (wherein B is N and A, K, and Q are as described in the Summary) is described in SCHEME 9. The appropriate formula 5 sulfonamide or amide is alkylated using the conditions described in SCHEMES 1 and 2 with an electrophile which contains an aromatic bromide or iodide or a ring system which contains a vinyl bromide or iodide ($Ar_1$) to provide formula 53 compounds. Suzuki-type coupling of the formula 53 compound with an aryl boronic acid ($Ar_2$) provides formula 53a compounds (for a review of the Suzuki reaction see A. R. Martin and Y. Yang in Acta Chem. Scand. 1993, 47, 221). The coupling reaction is achieved using about two equivalents of a base, such as sodium carbonate, potassium carbonate, sodium hydroxide, thallium hydroxide, potassium phosphate, or sodium methoxide, in the presence of a palladium catalyst, such as tetrakis(triphenylphosphine)palladium(0), palladium acetate, palladium chloride, tris(dibenzylideneacetone)dipalladium(0) or [1,4-bis(diphenylphosphine)butane]palladium(0). The reaction may be run in aqueous alcoholic solvents (methanol or ethanol), aqueous tetrahydrofuran, aqueous acetone, aqueous glycol dimethyl ether, or aqueous benzene at temperatures ranging from about 0° C. to about 120° C. When $Ar_1$ represents a partially saturated ring, if appropriate, reduction of the ring to provide a saturated ring system may be performed at this point. Conditions to accomplish this transformation involve hydrogenation in the presence of a catalyst such as palladium or platinum in an alcoholic solvent (ethanol or methanol) and/or ethyl acetate. Ester hydrolysis of formula 53a compounds, if desired, provides the corresponding acid. The resulting acids may contain functional groups on either of the ring systems ($Ar_1$ or $Ar_2$) which can be modified using methods known to those skilled in the art. Examples of such modifications are shown in SCHEME 10.

SCHEME 9

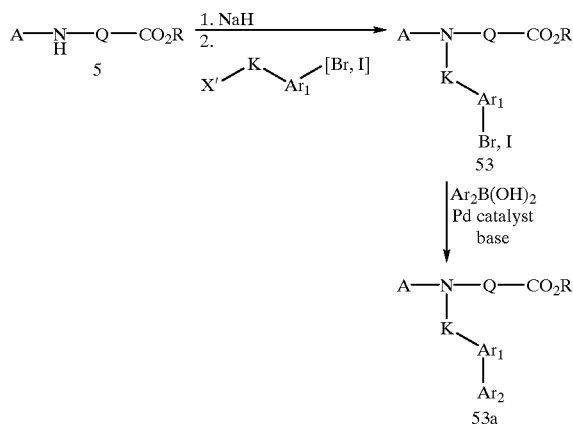

Formula 54 compounds which contain an aldehyde functional group can be prepared using methods described in SCHEMES 8 and 9. According to SCHEME 10, treatment of the formula 54 compound with an appropriate organometallic reagent (LMetal), such as an organolithium or Grignard reagent, in an aprotic solvent such as diethyl ether or tetrahydrofuran at a temperature of about −78° C. to about 80° C., followed by hydrolysis of the ester, provides formula 56 compounds (wherein B is N and A, Q and K are as described in the Summary and $Ar_1$ and $Ar_2$ are as described in SCHEME 9). Alternatively, reduction of the aldehyde followed by hydrolysis provides formula 55 compounds.

SCHEME 10

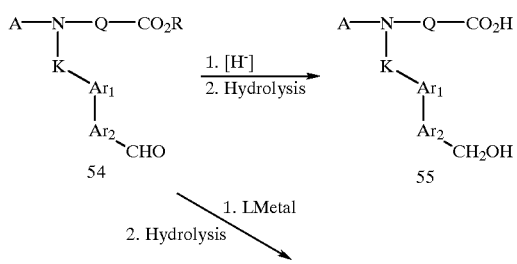

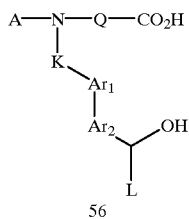

Alternatively, another method of preparing certain Formula I compounds (i.e., formula 57 compounds wherein B is N and A, K, and Q are as described in the Summary and R is as described in SCHEMES 1 and 2 and accordingly the corresponding acids) is described in SCHEME 11. The formula 58 starting alcohol can be prepared using the methods described in SCHEMES 1 and 2. Intermediate 58 is coupled with a variety of aryl alcohols (M represents an aromatic ring) using Mitsonobu conditions (for a review see O. Mitsonobu, Synthesis, 1, 1981). Typically the coupling is achieved by addition of a coupling agent such as triphenylphosphine and diethyl azodicarboxylate (DEAD) or diisopropyl azodicarboxylate in inert solvents such as methylene chloride or tetrahydrofuran at a temperature of about 0° C. to about 80° C. If desired, subsequent hydrolysis yields the corresponding acid.

SCHEME 11

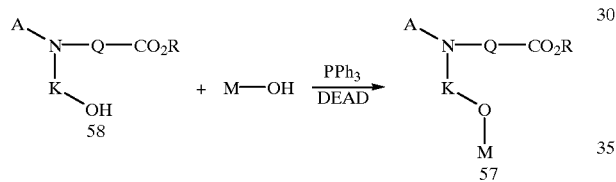

Alternatively, another method of preparing certain Formula I compounds (i.e., formula 106 compounds wherein B is N and A, K, and M are as described in the Summary and R is as described in SCHEMES 1 and 2 and accordingly, the corresponding acids) is described in SCHEME 12. A formula 102 compound is added to a formula 105 compound (wherein the X is an aromatic ring such as a benzene ring or a thiophene ring) in the presence of a Lewis acid such as titanium tetrachloride or a mineral acid such as hydrochloric acid. If desired the formula 106 ester can be converted to the corresponding acid by hydrolysis or deprotection.

SCHEME 12

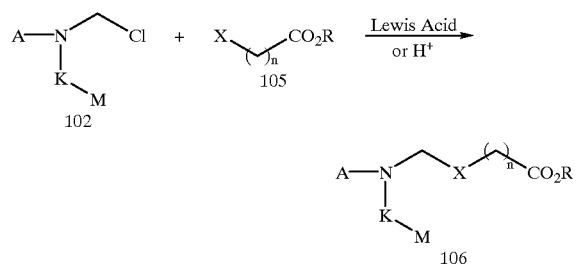

Alternatively, another method of preparing certain Formula I compounds (i.e., formula 107 or 108 compounds wherein B is N and A, and Q are as described in the Summary and accordingly, the corresponding acids) is described in SCHEME 13. Formula 104 chloromethyl compounds are treated with the appropriate substituted aromatic ring system, M, such as 4-ethoxybenzene or thiophene in the presence of a Lewis acid such as titanium tetrachloride or a mineral acid such as hydrochloric acid in an aprotic solvent such as chloroform at a temperature of about 0C to about 80° C to yield the formula 107 compound which may subsequently be hydrolyzed or deprotected as described above to yield the corresponding acid. Alternatively, formula 104 chloromethyl compounds can be treated with a Lewis acid such as titanium tetrachloride and an appropriately substituted vinyl silane in an aprotic solvent such as methylene chloride at a temperature of about −50° C. to about 50° C. to give formula 108 compounds which may subsequently be hydrolyzed or deprotected as described above to yield the corresponding acid. If desired, reduction of the double bond can be accomplished using conditions described in SCHEME 7.

SCHEME 13

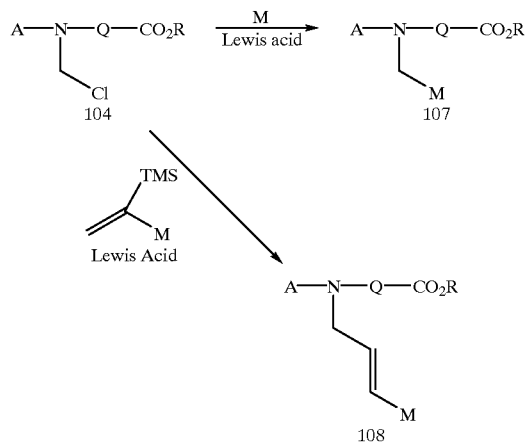

Alternatively, another method of preparing certain Formula I compounds (i.e., formula 109 compounds, wherein B is N and A, Q, R and M are as described above, and accordingly, the corresponding acids) is described in SCHEME 14. Formula 104 chloromethyl compounds are treated with a Lewis acid such as titanium tetrachloride and an appropriately substituted allyl silane in an aprotic solvent such as chloroform at a temperature of about 0° C. to about 80° C. to give formula 109 compounds which may subsequently be hydrolyzed or deprotected as described above.

SCHEME 14

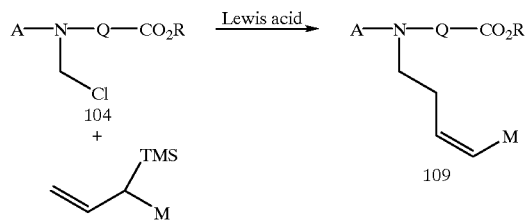

Alternatively, another method of preparing certain Formula I compounds (i.e., formula 112 compounds, wherein B is N and A, Q, R and M are as described above, and accordingly, the corresponding acids) is described in SCHEME 15. Formula 104 chloromethyl compounds are treated with a formula 111 sulfonic acid in the presence of a base such as triethylamine in an aprotic solvent such as chloroform at a temperature of about −30° C. to about 50° C. to give formula 112 compounds which may subsequently be hydrolyzed or deprotected as described above to yield the corresponding acid.

SCHEME 15

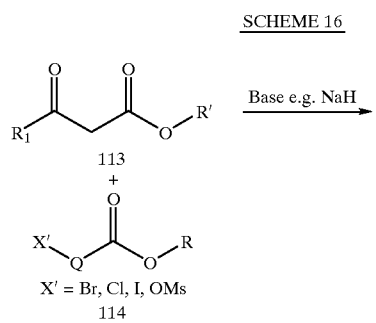

Formula I compounds (wherein B is C(H) and Q, M and K are as described in the Summary, R' is a small chain alkyl group, and R₁ represents the alkyl groups on A as described in the Summary) can be prepared according to SCHEME 16. Formula 113 beta-ketoesters are alkylated sequentially with formula 114 compounds followed by alkylation of formula 116 compounds to give formula 117 compounds (J. Med. Chem. 26, 1993, p335–41). Alkylations can be carried out in a suitable solvent such as DMF, THF, ether, or benzene using an appropriate base such as sodium hydride, LDA, or potassium carbonate at a temperature of about −78° C. to about 80° C. The resulting formula 117 disubstituted keto esters are hydrolyzed and decarboxylated to give the corresponding formula 118 compound by using an aqueous base such as sodium hydroxide to hydrolyze the ester, followed by an acidic quench such as aqueous hydrochloric acid to effect decarboxylation.

SCHEME 16

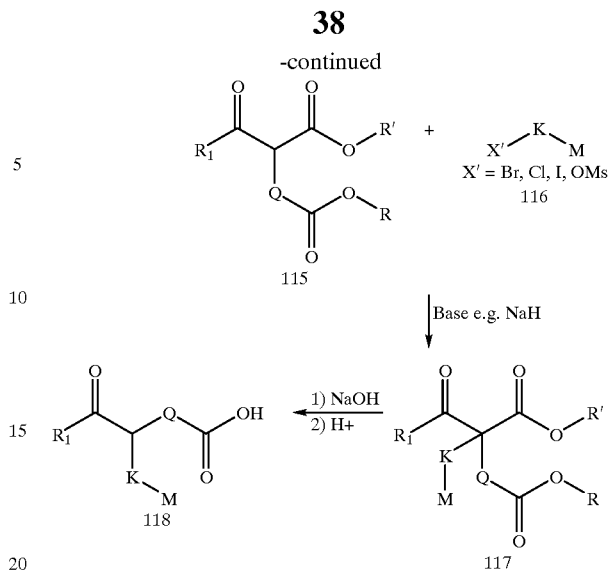

Alternatively, Formula I compounds (wherein B is C(H) and Q, M and k are as described in the Summary, R' is as described above, and RI represents the alkyl groups on A as described in the Summary) may be prepared according to SCHEME 17. Sequential alkylation of a malonate derivative of formula 119 provides the formula 121 dialkylated species. Deprotection of the ester group by treatment with a strong acid such as TFA or HCl in ethanol at a temperature of about −20° C. to about 50° C. leads to the formula 122 decarboxylated product. Conversion of the acid to an acid chloride using thionyl chloride or oxalyl chloride in an aprotic solvent at a temperature of about −78° C. to about 50° C. or to a Weinreb amide using methoxymethyl amine in the presence of a suitable coupling agent such as DCC or DEC in an aprotic solvent at a temperature of about −30° C. to about 50° C. provides formula 123 compounds. Formula 123 are suitable substrates for addition of various organometallic species (e.g., grignard reagents, organo-cadmium reagents) which after hydrolysis of the terminal ester provide the keto-acid compounds of formula 118.

Alternatively formula 118 compounds can be prepared using methods described previously (e.g. see SCHEMES 7, 8, 9, 10, and 11) where one or both of the side chains are further functionalized after attachment.

SCHEME 17

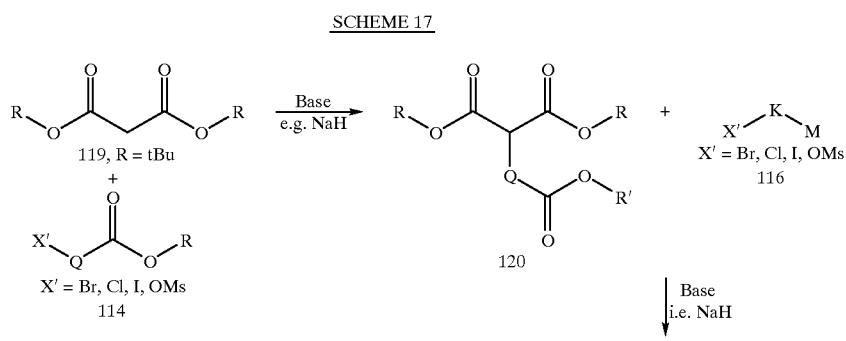

-continued

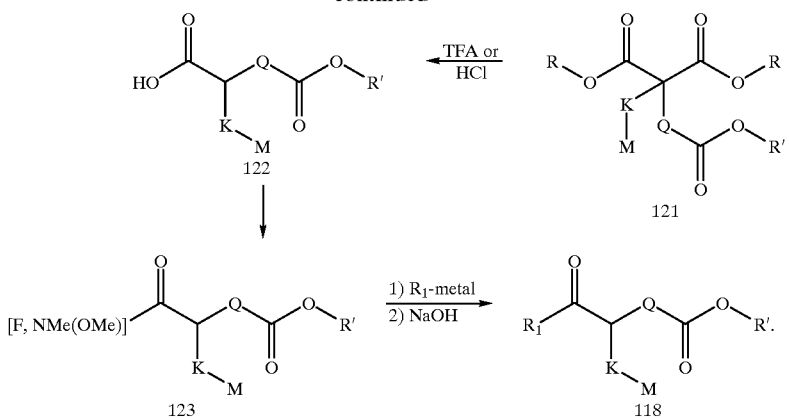

Preparations

Amines, Amides and Sulfonamides

Certain amines described by formulas 21, 22, and 23 (wherein W and Z are as described in the Summary and X and M are aromatic or saturated ring systems may be prepared according to SCHEME 18. Formula 25, 26 and 27 alkynyl amines are prepared by coupling a formula 24 alkynyl sulfonamide or amide to an aromatic or vinyl halide, preferably an aromatic or vinyl bromide or iodide (wherein W and Z are as defined above and where X and M represent an aromatic ring or a partially saturated ring system). The coupling is typically accomplished in the presence of copper iodide, a palladium catalyst, such as palladium chloride, bis(triphenylphosphine)palladium dichloride, or tetrakis(triphenylphosphine)palladium(0), and an amine such as triethylamine, diisopropylamine, or butylamine in an aprotic solvent such as acetonitrile at a temperature of about 0° C. to about 100° C. The resulting formula 25, 26 and 27 alkynes can be converted to the corresponding formula 21, 22 or 23 alkanes, via hydrogenation in the presence of a palladium or platinum catalyst and in solvents such as methanol, ethanol, and/or ethyl acetate at a temperature of about 0° C. to about 50° C. Alternatively, one can convert the alkyne to the cis-alkene using the Lindlar catalyst (Pd—CaCO$_3$—PbO). In the case where M represents a partially saturated ring system, hydrogenation will convert M to a fully saturated ring system. Alkylation and deprotection as described in SCHEMES 1 and 2 affords the corresponding Formula I compounds.

SCHEME 18

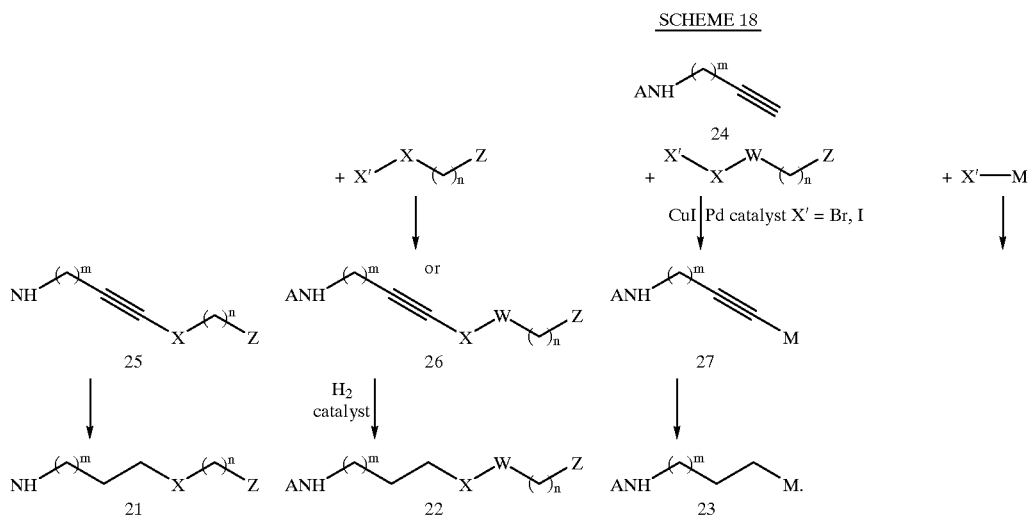

According to SCHEME 19 formula 33 compounds (wherein A and X are as described in the Summary) can be prepared from a suitable formula 32 amine (e.g., methoxyarylalkylamine). Formula 32 amines are commercially available or can be prepared by methods known to those skilled in the art (for example, see SCHEME 4) and are converted to formula 31 sulfonamides or amides using methods, for example, described in SCHEME 3 and 4. The resulting formula 31 aromatic methyl ether is deprotected with reagents such as boron tribromide, pyridinium hydrochloride, hydrogen bromide/acetic acid, or other reagents as described in Protecting Groups in Organic Synthesis, Second Edition, T. W. Greene and P. G. M. Wuts, John Wiley and Sons, Inc., 1991. Alkylation with a bromoalkylester using a mild base such as potassium carbonate in an aprotic solvent such as dimethylformamide or acetone at a temperature of about 0° C. to about 100° C. generates the desired formula 33 amide or sulfonamide.

SCHEME 19

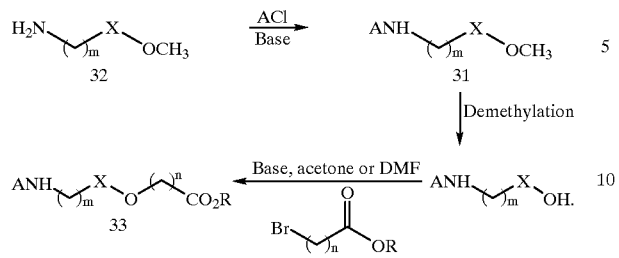

Alkylating Agents

Numerous methods exist for the synthesis of the desired alkylating agents used in the above procedures and are known to those skilled in the art (see "The Chemistry of the Carbon-Halogen Bond," Ed. S. Patai, J. Wiley, New York, 1973 and "The Chemistry of Halides, Pseudo-Halides, and Azides," Eds. S. Patai and Z. Rappaport, J. Wiley, New York, 1983). Some examples are shown in SCHEMES 20–26. As shown in SCHEME 20, tolyl or allylic substrates can be converted via halogenation to benzylic or allylic bromides (wherein M, X, W and Z are as described in the Summary). This reaction is typically performed with N-bromosuccinimide (NBS) in the presence of a radical initiator such as AIBN or a peroxide, preferably benzoyl peroxide. Alternatively, the reaction can be initiated with light. The reaction is done in an inert solvent such as carbon tetrachloride or chloroform at a temperature of about 50° C. to about 100° C.

SCHEME 20

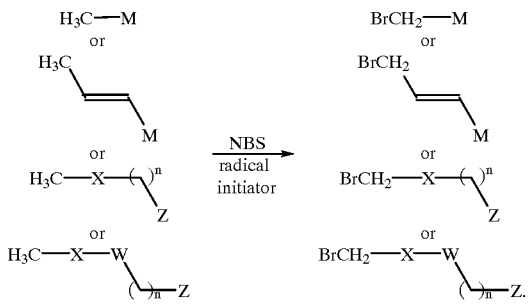

SCHEME 21 demonstrates the synthesis of alkylating agents useful for preparing Formula I compounds where M represents a biaryl or aryl cyclic group. Suzuki-type coupling of an aryl iodide or bromide or a ring system containing a vinyl bromide or iodide ($Ar_2$) with a methylaryl boronic acid ($Ar_1$) using the conditions described in SCHEME 9 provides formula 34 compounds. In the case where a vinyl bromide or iodide is used, formula 34 compounds can be reduced to generate a fully saturated ring. The reduction is accomplished by hydrogenation in the presence of palladium or platinum catalysts typically in protic solvents (methanol or ethanol), tetrahydrofuran, or ethyl acetate. Halogenation of the methyl group using reagents and conditions as described in SCHEME 20 provides formula 35 alkylating agents.

SCHEME 21

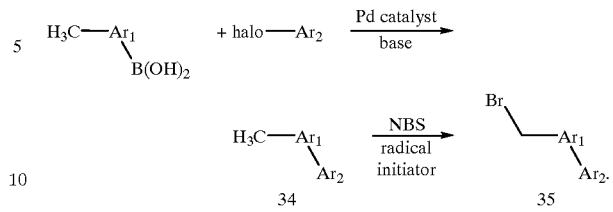

Another common method for accessing alkyl halides is by halogenation of an alcohol or an alcohol derivative. Alcohols are obtained from commercial sources or can be prepared using methods known to those skilled in the art. For example, in SCHEME 22, a carboxylic acid or ester is reduced to the alcohol using reagents such as sodium borohydride, lithium aluminum hydride, borane-tetrahydrofuran complex, borane-methyl sulfide complex, etc. The corresponding alkyl chlorides are typically prepared from the alcohols with reagents such as hydrogen chloride, thionyl chloride, phosphorous pentachloride, phosphorous oxychloride, or triphenylphosphine/carbon tetrachloride. For the preparation of alkyl bromides, the alcohol is commonly treated with reagents such as hydrogen bromide, phosphorous tribromide, triphenylphosphine/bromine, or carbonyldiimidazole/allyl bromide (Kamijo, T., Harada, H., Iizuka, K. Chem. Pharm. Bull. 1983, 38, 4189). To access alkyl iodides, one typically reacts the alcohol with reagents such as triphenylphosphine/iodine/imidazole or hydrogen iodide. Alkyl chlorides can be converted to the more reactive alkyl bromides or alkyl iodides by treatment with an inorganic salt such as sodium bromide, lithium bromide, sodium iodide, or potassium iodide in solvents such as acetone or methyl ethyl ketone. Alkyl sulfonates can also be used as electrophiles or can be converted to alkyl halides. Sulfonates are prepared from the alcohol using a mild base such as triethylamine or pyridine and a sulfonyl chloride in an inert solvent such a methylene chloride or diethyl ether. Conversion to the halide is accomplished by treatment with an inorganic halide (sodium iodide, sodium bromide, potassium iodide, potassium bromide, lithium chloride, lithium bromide, etc) or a tetrabutylammonium halide.

SCHEME 22

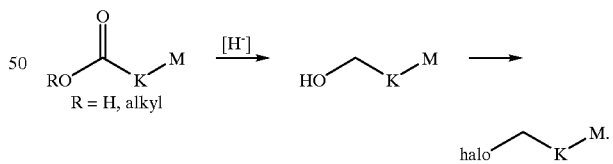

Cinnamic acids or esters are commonly available from commercial sources and can by converted to formula 37 or 38 alkylating agents as follows (see SCHEME 23). The cinnamic acid or ester derivatives are reduced by hydrogenation in the presence of palladium or platinum catalysts typically in protic solvents (e.g., methanol or ethanol), tetrahydrofuran, or ethyl acetate. Reduction and conversion to the alkyl halide or sulfonate as described in SCHEME 22 provides formula 38. Where appropriate, the cinnamic acids or esters are converted directly to formula 39 alcohols by treatment with reagents such as lithium aluminum hydride in inert solvents such as tetrahydrofuran and diethyl ether.

Alternatively, the cinnamic acid or ester can be reduced to the formula 40 allylic alcohol using reagents such as lithium aluminum hydride/aluminum chloride, diisobutylaluminum hydride, or lithium borohydride. Conversion to the allylic halide or sulfonate as described in SCHEME 22 provides formula 37 reagents.

SCHEME 23

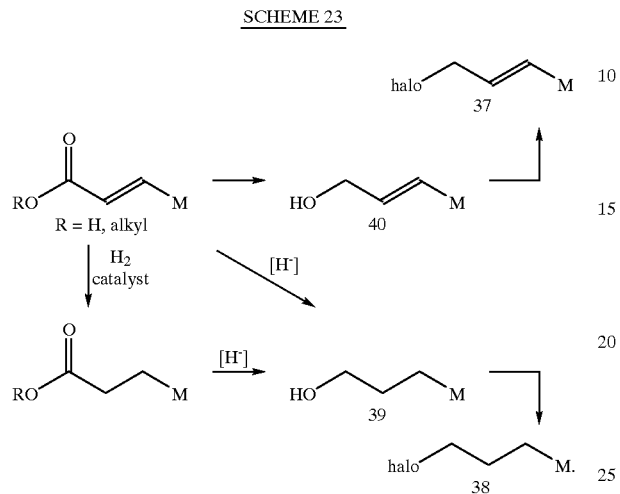

The preparation of formula 41 alkylating agents (wherein W and M are as described in the Summary above) are described in SCHEME 24. Formula 42 compounds are alkylated with a variety of bases the choice of which is dependent on the nature of W and M. Some preferred bases are sodium hydroxide, sodium hydride, lithium diisopropylamide, lithium bis(trimethylsilyl)amide, potassium bis(trimethylsilyl)amide and potassium tert-butoxide, etc. Treatment of the resulting anion with a variety of dialkylhalides generates the desired formula 41 alkylating agents. For the preparation of compounds where W represents an oxygen and M is an aromatic ring, the preferred conditions involve formation of the alkoxide anion with sodium hydroxide followed by addition of a dihaloalkane, e.g. dibromoalkane. The reaction is normally performed in water at about 75° C. to about 125° C.

SCHEME 24

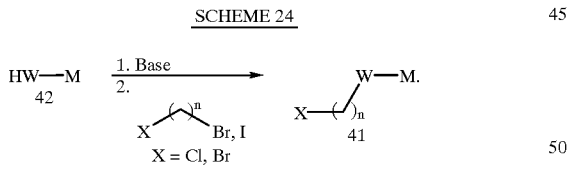

Aldehydes useful for the chemistry described in SCHEME 5 are available from commercial sources or can be prepared from available intermediates using methods known to those skilled in the art. SCHEME 25 demonstrates an exemplary method used to prepare formula 43 hydroxy aldehydes (where M in SCHEME 5 contains a hydroxy substituted alkyl group). Treatment of a dialdehyde, where one of the aldehydes is protected as a formula 44 acetal (wherein the OR groups are conventional substituents used in an acetal protecting group), with an organometallic reagent (LMetal), preferably an organolithium or Grignard reagent, in an inert solvent such as tetrahydrofuran or diethyl ether, provides formula 45 compounds. Subsequent acetal hydrolysis under mildly acidic conditions, e.g. dilute hydrogen chloride, Amberlyst-15 resin, silica gel, or other reagents as described in "Protecting Groups in Organic Synthesis," Second Edition, T. W. Greene and P. G. M. Wuts, John Wiley and Sons, Inc., 1991 provides the desired formula 43 hydroxy aldehydes.

SCHEME 25

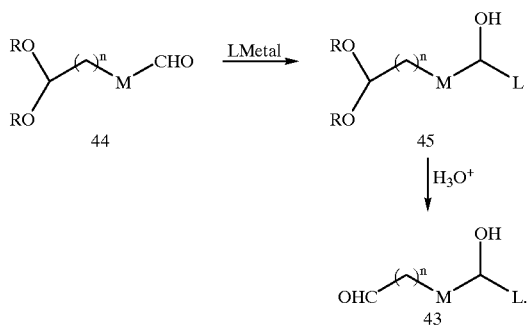

Chloromethyl Intermediates

Intermediate chloromethyl compounds can be prepared as described in SCHEMES 26 and 27. In general, the appropriate formula 101 or 103 sulfonamide or carboxamide is treated with a formaldehyde equivalent such as paraformaldehyde in an inert organic solvent such as methylene chloride or chloroform with a suitable catalyst such as HCl, zinc chloride or trimethylsilyl chloride at temperatures ranging from about 0° C. to about 60° C. to give the formula 102 and 104 chloromethyl derivatives, respectively.

SCHEME 26

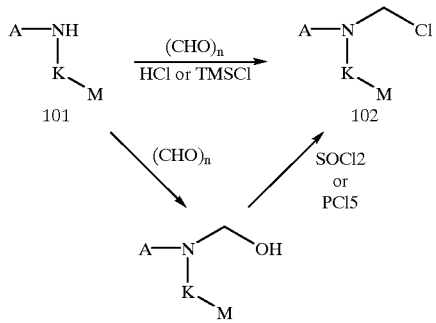

SCHEME 27

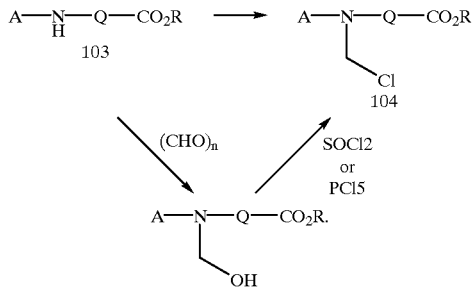

Some of the preparation methods useful for the preparation of the compounds described herein may require protection of remote functionality (e.g., primary amine, secondary amine, carboxyl in Formula I precursors). The need for such protection will vary depending on the nature of the remote functionality and the conditions of the preparation methods. The need for such protection is readily determined by one skilled in the art. The use of such protection/deprotection methods is also within the skill in the art. For a general description of protecting groups and their use, see T. W. Greene, *Protective Groups in Organic Synthesis,* John Wiley & Sons, New York, 1991.

The starting materials and reagents for the above described compounds, are also readily available or can be easily synthesized by those skilled in the art using conventional methods of organic synthesis. For example, many of the compounds used therein, are related to, or are derived from compounds found in nature, in which there is a large scientific interest and commercial need, and accordingly many such compounds are commercially available or are reported in the literature or are easily prepared from other commonly available substances by methods which are reported in the literature. Such compounds include, for example, prostaglandins.

Some of the compounds of this invention have asymmetric carbon atoms and therefore are enantiomers or diastereomers. Diasteromeric mixtures can be separated into their individual diastereomers on the basis of their physical chemical differences by methods known per se., for example, by chromatography and/or fractional crystallization. Enantiomers can be separated by converting the enantiomeric mixture into a diasteromeric mixture by reaction with an appropriate optically active compound (e.g., alcohol), separating the diastereomers and converting (e.g., hydrolyzing) the individual diastereomers to the corresponding pure enantiomers. All such isomers, including diastereomers, enantiomers and mixtures thereof are considered as part of this invention.

Many of the compounds of this invention are acidic and they form a salt with a pharmaceutically acceptable cation. Some of the compounds of this invention are basic and they form a salt with a pharmaceutically acceptable anion. All such salts are within the scope of this invention and they can be prepared by conventional methods. For example, they can be prepared simply by contacting the acidic and basic entities, usually in a stoichiometric ratio, in either an aqueous, non-aqueous or partially aqueous medium, as appropriate. The salts are recovered either by filtration, by precipitation with a non-solvent followed by filtration, by evaporation of the solvent, or, in the case of aqueous solutions, by lyophilization, as appropriate.

In addition, when the compounds of this invention form hydrates or solvates they are also within the scope of the invention.

The compounds of this invention are all adapted to therapeutic use as agents that stimulate bone formation and increase bone mass and prevent bone loss in mammals, particularly humans. Since bone formation is closely related to the development of osteoporosis and bone related disorders, these compounds, by virtue of their action on bone, prevent, arrest and/or regress osteoporosis.

The utility of the compounds of the present invention as medical agents in the treatment of conditions which present with low bone mass (e.g., osteoporosis) in mammals (e.g. humans, particularly the female) is demonstrated by the activity of the compounds of this invention in the in vivo assay, the EP2 selective receptor binding assay, the Cyclic AMP assay and the Fracture healing assay (all of which are described below). Such assays also provide a means whereby the activities of the compounds of this invention can be compared to each other and with the activities of other known compounds. The results of these comparisons are useful for determining dosage levels in mammals, including humans, for the treatment of such diseases.

In Vivo Assay

The activity of anabolic bone agents in stimulating bone formation and increasing bone mass can be tested in intact male or female rats, sex hormone deficient male (orchidectomy) or female (ovariectomy) rats.

Male or female rats at different ages (such as 3 months of age) can be used in the study. The rats are either intact or castrated (ovariectomized or orchidectomized), and subcutaneously injected or gavaged with EP2 agonists at different doses (such as 1,3, or 10 mg/kg/day) 30 days. In the castrated rats, treatment is started at the next day after surgery (for the purpose of preventing bone loss) or at the time bone loss has already occured (for the purpose of restoring bone mass). During the study, all rats are allowed free access to water and a pelleted commercial diet (Teklad Rodent Diet #8064, Harlan Teklad, Madison, Wis.) containing 1.46% calcium, 0.99% phosphorus and 4.96 IU/g of Vit.$D_3$. All rats are given subcutaneous injections of 10 mg/kg calcein on days 12 and 2 before sacrifice. The rats are sacrificed. The following endpoints are determined:

Femoral Bone Mineral Measurements

The right femur from each rat is removed at autopsy and scanned using dual energy x-ray absorptiometry (DXA, QDR 1000/W, Hologic Inc., Waltham, Mass.) equipped with "Regional High Resolution Scan" software (Hologic Inc., Waltham, Mass.). The scan field size is 5.08×1.902 cm, resolution is 0.0254×0.0127 cm and scan speed is 7.25 mm/second. The femoral scan images are analyzed and bone area, bone mineral content (BMC), and bone mineral density (BMD) of whole femora (WF), distal femoral metaphyses (DFM), femoral shaft (FS), and proximal femora (PF) are determined.

Tibial Bone Histomorphometric Analyses

The right tibia is removed at autopsy, dissected free of muscle, and cut into three parts. The proximal tibia and the tibial shaft are fixed in 70% ethanol, dehydrated in graded concentrations of ethanol, defatted in acetone, then embedded in methyl methacrylate (Eastman Organic Chemicals, Rochester, N.Y.).

Frontal sections of proximal tibial metaphyses at 4 and 10 $\mu$m thickness are cut using Reichert-Jung Polycut S microtome. The 4 $\mu$m sections are stained with modified Masson's Trichrome stain while the 10 $\mu$m sections remained unstained. One 4 $\mu$m and one 10 $\mu$m sections from each rat are used for cancellous bone histomorphometry.

Cross sections of tibial shaft at 10 $\mu$m thickness are cut using Reichert-Jung Polycut S microtome. These sections are using for cortical bone histomorphometric analysis.

Cancellous Bone Histomorphometry

A Bioquant OS/2 histomorphometry system (R&M biometrics, Inc., Nashville, Tenn.) is used for the static and dynamic histomorphometric measurements of the secondary spongiosa of the proximal tibial metaphyses between 1.2 and 3.6 mm distal to the growth plate-epiphyseal junction. The first 1.2 mm of the tibial metaphyseal region needs to be omitted in order to restrict measurements to the secondary spongiosa. The 4 $\mu$m sections are used to determine indices related to bone volume, bone structure, and bone resorption, while the 10 $\mu$m sections are used to determine indices related to bone formation and bone turnover.

I) Measurements and Calculations Related to Trabecular Bone Volume and Structure (1) Total metaphyseal area (TV, mm$^2$): metaphyseal area between 1.2 and 3.6 mm distal to the growth plate-epiphyseal junction. (2) Trabecular bone area (BV, mm$^2$): total area of trabeculae within TV. (3) Trabecular bone perimeter (BS, mm): the length of total perimeter of trabeculae. (4) Trabecular bone volume (BV/TV, %): BV/TV× 100. (5) Trabecular bone number (TBN, #/mm): 1.199/2× BS/TV. (6) Trabecular bone thickness (TBT, $\mu$m): (2000/ 1.199)×(BV/BS). (7) Trabecular bone separation (TBS, $\mu$m): (2000×1.199)×(TV-BV).

II) Measurements and Calculations Related to Bone Resorption (1) Osteoclast number (OCN, #): total number of osteoclast within total metaphyseal area. (2) Osteoclast perimeter (OCP, mm): length of trabecular perimeter covered by osteoclast. (3) Osteoclast number/mm (OCN/mm, #/mm): OCN/BS. (4) Percent osteoclast perimeter (%OCP, %): OCP/BS×100.

III) Measurements and Calculations Related to Bone Formation and Turnover (1) Single-calcein labeled perimeter (SLS, mm): total length of trabecular perimeter labeled with one calcein label. (2) Double-calcein labeled perimeter (DLS, mm): total length of trabecular perimeter labeled with two calcein labels. (3) Inter-labeled width (ILW, $\mu$m): average distance between two calcein labels. (4) Percent mineralizing perimeter (PMS, %): (SLS/2+DLS)/BS×100. (5) Mineral apposition rate (MAR, $\mu$m/day): ILW/label interval. (6) Bone formation rate/surface ref. (BFR/BS, $\mu$m$^2$/d/$\mu$m): (SLS/2+ DLS)×MAR/BS. (7) Bone turnover rate (BTR, %/y): (SLS/ 2+DLS)×MAR/BV×100.

Cortical Bone Histomorphometry

A Bioquant OS/2 histomorphometry system (R&M biometrics, Inc., Nashville, Tenn.) is used for the static and dynamic histomorphometric measurements of tibial shaft cortical bone. Total tissue area, marrow cavity area, periosteal perimeter, endocortical perimeter, single labeled perimeter, double labeled perimeter, and interlabeled width on both periosteal and endocortical surface are measured, and cortical bone area (total tissue area×marrow cavity area), percent cortical bone area (cortical area/total tissue area×100), percent marrow area (marrow cavity area/total tissue area×100), periosteal and endocortical percent labeled perimeter [(single labeled perimeter/2+double labeled perimeter)/total perimeter×100], mineral apposition rate (interlabeled width/intervals), and bone formation rate [mineral apposition rate×[(single labeled perimeter/2+ double labeled perimeter)/total perimeter] are calculated.

Statistics

Statistics can be calculated using StatView 4.0 packages (Abacus Concepts, Inc., Berkeley, Calif.). The analysis of variance (ANOVA) test followed by Fisher's PLSD are used to compare the differences between groups.

Determination of cAMP Elevation in 293-S Cell Lines Stably Overexpressing Recombinant Human EP2 and EP4 Receptors cDNAs representing the complete open reading frames of the human EP2 and EP4 receptors are generated by reverse transcriptase polymerase chain reaction using oligonucleotide primers based on published sequences (1,2) and RNA from primary human kidney cells (EP2) or primary human lung cells (EP4) as templates. cDNAs are cloned into the multiple cloning site of pcDNA3 (Invitrogen) and used to transfect 293-S human embryonic kidney cells via calcium phosphate co-precipitation. G418-resistent colonies are expanded and tested for specific [3-H]PGE2 binding. Transfectants demonstrating high levels of specific [3-H]PGE2 binding are further characterized by scatchard analysis to determine Bmax and Kds for PGE2. The lines selected for compound screening have approximately 338,400 receptors per cell and a Kd=12 nM for PGE2 (EP2), and approximately 256,400 receptors per cell and a Kd=2.9 nM for PGE2 (EP4). Constituitive expression of both receptors in parental 293-S cells is negligible. Cells are maintained in RPMI supplemented with fetal bovine serum (10% final) and G418 (700 ug/ml final).

cAMP responses in the 293-S/EP2 and 293-S/EP4 lines are determined by detaching cells from culture flasks in 1 ml of Ca++ and Mg++ deficient PBS via vigorous pounding, adding serum-free RPMI to a final concentration of 1×10$^6$ cells/ml, and adding 3-isobutyl-1-methylxanthine (IBMX) to a final concentration of 1 mM. One milliliter of cell suspension is immediately aliquoted into individual 2 ml screwcap microcentrifuge and incubated for 10 minutes, uncovered, at 37 ° C., 5% $CO_2$, 95% relative humidity. The compound to be tested is then added to cells at 1:100 dilutions such that final DMSO or ethanol concentrations is 1%. Immediately after adding compound, the tubes are covered, mixed by inverting two times, and incubated at 37° C. for 12 minutes. Samples are then lysed by incubation at 100° C. for 10 minutes and immediately cooled on ice for 5 minutes. Cellular debris is pelleted by centrifugation at 1000×g for 5 minutes, and cleared lysates are transferred to fresh tubes. cAMP concentrations are determined using a commercially available cAMP radioimmunoassay kit (NEK-033, NEN/DuPont) after diluting cleared lysates 1:10 in cAMP RIA assay buffer. Typically, one treats cells with 6–8 concentrations of the compound to be tested in 1 log increments. EC50 calculations are performed on a Hewlett Packard 32SII hand-held calculator using linear regression analysis on the linear portion of the dose response curves.

References

1. Regan, J. W. Bailey, T. J. Pepperl, D. J. Pierce, K. L. Bogardus, A. M. Donello, J. E. Fairbaim, C. E. Kedzie, K. M. Woodward, D. F. and Gil, D. W. 1994 Cloning of a Novel Human Prostaglandin Receptor with Characteristics of the Pharmaclogically Defined EP$_2$ Subtype. Mol. Pharmacology 46:213–220.
2. Bastien, L., Sawyer, N., Grygorczyk, R., Metters, K., and Adam, M. 1994 Cloning, Functional Expression, and Characterization of the Human Prostaglandin E2 Receptor EP2 Subtype. J. Biol. Chem. Vol 269, 16:11873–11877.

Assay for Binding to Prostaglandin E2 Receptors
Membrane Preparation

All operations are performed at 4° C. Transfected cells expressing prostaglandin E2 type 1 receptors (EP1), type 2 (EP2), type 3 (EP3) or type 4 (EP4) receptors are harvested and suspended to 2 million cells per ml in Buffer A [50 mM Tris-HCl (pH 7.4), 10 mM $MgCl_2$, 1 mM EDTA, 1 mM Pefabloc peptide, (Sigma, St. Louis, Mo.), 10 uM Phosporamidon peptide, (Sigma, St. Louis, Mo.), 1 $\mu$M Pepstatin A peptide, (Sigma, St. Louis, Mo.), 10 uM Elastatinal peptide, (Sigma, St. Louis, Mo.), 100 uM Antipain peptide, (Sigma, St. Louis, Mo.)]. These are lysed by sonification with a Branson Sonifier (Model #250, Branson Ultrasonics Corporation, Danbury, Conn.) in 2 fifteen second bursts. Unlysed cells and debris are removed by centrifugation at 100×g for 10 min. Membranes are then harvested by centrifugation at 45,000×g for 30 minutes. Pelleted membranes are resuspended to 3–10 mg protein per ml, protein concentration being determined according to the method of Bradford [Bradford, M., Anal. Biochem., 72, 248 (1976)]. Resuspended membranes are then stored frozen at −80° C. until use.

Binding Assay

Frozen membranes prepared as above are thawed and diluted to 1 mg protein per ml in Buffer A. One volume of membrane preparation is combined with 0.05 volume test compound or buffer and one volume of 3 nM 3H-prostaglandin E2 (#TRK 431, Amersham, Arlington Heights, Ill.) in Buffer A. The mixture (205 μL total volume) is incubated for 1 hour at 25° C. The membranes are then recovered by filtration through type GF/C glass fiber filters (#1205-401, Wallac, Gaithersburg, Md.) using a Tomtec harvester (Model Mach II/96, Tomtec, Orange, Conn.). The membranes with bound 3H-prostaglandin E2 are trapped by the filter, the buffer and unbound 3H-prostaglandin E2 pass through the filter into waste. Each sample is then washed 3 times with 3 ml of [50 mM Tris-HCl (pH 7.4), 10 mM $MgCl_2$, 1 mM EDTA]. The filters are then dried by heating in a microwave oven. To determine the amount of 3H-prostaglandin bound to the membranes, the dried filters are placed into plastic bags with scintillation fluid and counted in a LKB 1205 Betaplate reader (Wallac, Gaithersburg, Md.). IC50s are determined from the concentration of test compound required to displace 50% of the specifically bound 3H-prostaglandin E2.

Fracture Healing

Assay for Effects on Fracture Healing after Systemic Administration

Fracture Technique

Sprage-Dawley rats at 3 months of age are anesthetized with Ketamine. A 1 cm incision is made on the anteromedial aspect of the proximal part of the right tibia or femur. The following describes the tibial surgical technique. The incision is carried through to the bone, and a 1 mm hole is drilled 4 mm proximal to the distal aspect of the tibial tuberosity 2 mm medial to the anterior ridge. Intramedullary nailing is performed with a 0.8 mm stainless steel tube (maximum load 36.3 N, maximum stiffness 61.8 N/mm, tested under the same conditions as the bones). No reaming of the medullary canal is performed. A standardized closed fracture is produced 2 mm above the tibiofibular junction by three-point bending using specially designed adjustable forceps with blunt jaws. To minimize soft tissue damage, care is taken not to displace the fracture. The skin is closed with monofilament nylon sutures. The operation is performed under sterile conditions. Radiographs of all fractures are taken immediately after nailing, and animals with fractures outside the specified diaphyseal area or with displaced nails are excluded. The remaining animals are divided randomly into the following groups with 10–12 animals per each subgroup for testing the fracture healing. The first group receives daily gavage of vehicle (water: 100% Ethanol=95:5) at 1 ml/rat, while the others receive daily gavage from 0.01 to 100 mg/kg/day of the compound to be tested (1 m/rat) for 10, 20, 40 and 80 days.

At 10, 20, 40 and 80 days, 10–12 rats from each group are anesthetized with Ketamine and autopsied by exsanguination. Both tibiofibular bones are removed by dissection and all soft tissue is stripped. Bones from 5–6 rats for each group are stored in 70% ethanol for histological analysis, and bones from another 5–6 rats for each group are stored in a buffered Ringer's solution (+4° C., pH 7.4) for radiographs and biomechanical testing which is performed.

Histological Analysis

The methods for histologic analysis of fractured bone have been previously published by Mosekilde and Bak (The Effects of Growth Hormone on Fracture Healing in Rats: A Histological Descroption. Bone, 14:19–27, 1993). Briefly, the fracture side is sawed 8 mm to each side of the fracture line, embedded undecalcified in methylmethacrylate, and are frontal sections cut on a Reichert-Jung Polycut microtome (8 μm thick). Masson-Trichrome stained mid-frontal sections (including both tibia and fibula) are used for visualization of the cellullar and tissue response to fracture healing with and without treatment. Sirius red stained sections are used to demonstrate the characteristics of the callus structure and to differentiate between woven bone and lamellar bone at the fracture site. The following measurements are performed: (1) fracture gap—measured as the shortest distance between the cortical bone ends in the fracture, (2) callus length and callus diameter, (3) total bone volume area of callus, (4) bony tissue per tissue area inside the callus area, (5) fibrous tissue in the callus, (6) cartilage area in the callus.

Biomechanical Analysis

The methods for biomechanical analysis have been previously published by Bak and Andreassen (The Effects of Aging on Fracture Healing in Rats. Calcif Tissue Int 45:292–297, 1989). Briefly, radiographs of all fractures are taken prior to the biomechanical test. The mechanical properties of the healing fractures are analyzed by a destructive three- or four-point bending procedure. Maximum load, stiffness, energy at maximum load, deflection at maximum load, and maximum stress are determined.

Assay for Effects on Fracture Healing after Local Administration

Fracture Technique

Female or male beagle dogs at approximately 2 years of age are used in the study. Transverse radial fractures are produced by slow continuous loading in three-point bending as described by Lenehan et al. (Lenehan, T. M.; Balligand, M.; Nunamaker, D. M.; Wood, F. E.: Effects of EHDP on Fracture Healing in Dogs. J Orthop Res 3:499–507; 1985). The wire is pulled through the fracture site to ensure complete anatomical disruption of the bone. Thereafter, local delivery of EP2 agonists to the fracture site is achieved by slow release of compound delivered by injection of compound in gel or matrix, slow release pellets or Alzet minipumps for 10, 15, or 20 weeks.

Histological Analysis

The methods for histologic analysis of fractured bone have been previously published by Peter et al. (Peter, C. P.; Cook, W. O.; Nunamaker, D. M.; Provost, M. T.; Seedor, J. G.; Rodan, G. A. Effects of Alendronate on Fracture Healing and Bone Remodeling in Dogs. *J. Orthop. Res.* 14:74–70, 1996) and Mosekilde and Bak (The Effects of Growth Hormone on Fracture Healing in Rats: A Histological Description. *Bone,* 14:19–27, 1993). Briefly, the fracture side is sawed 3 cm to each side of the fracture line, embedded undecalcified in methylmethacrylate, and frontal sections are cut on a Reichert-Jung Polycut microtome (8 μm thick). Masson-Trichrome stained mid-frontal sections (including both tibia and fibula) are used for visualization of the cellullar and tissue response to fracture healing with and without treatment. Sirius red stained sections are used to demonstrate the characteristics of the callus structure and to differentiate between woven bone and lamellar bone at the fracture site. The following measurements are performed: (1) fracture gap—measured as the shortest distance between the cortical bone ends in the fracture, (2) callus length and callus diameter, (3) total bone volume area of callus, (4) bony tissue per tissue area inside the callus area, (5) fibrous tissue in the callus, (6) cartilage area in the callus.

Biomechanical Analysis

The methods for biomechanical analysis have been previously published by Bak and Andreassen (The Effects of Aging on Fracture Healing in Rats. Calcif Tissue Int 45:292–297, 1989) and Peter et al. (Peter, C. P.; Cook, W. O.; Nunamaker, D. M.; Provost, M. T.; Seedor, J. G.; Rodan, G. A. Effects of Alendronate on Fracture Healing and Bone Remodeling in Dogs. J. Orthop. Res. 14:74–70, 1996). Briefly, radiographs of all fractures are taken prior to the biomechanical test. The mechanical properties of the healing fractures are analyzed by a destructive three- or four-point bending procedures. Maximum load, stiffness, energy at maximum load, deflection at maximum load, and maximum stress are determined.

EXAMPLE 1 (EP2 AGONISTS)

According to the above protocols, the following compounds were tested for selective binding with prostaglandin E receptors (EP) (see protocol above). In addition, these compounds were also tested for their ability to stimulate cyclic AMP production (see protocol above), and stimulate bone formation in vivo (see protocol above).

I. (3-{[(4-Butyl-benzyl)-methanesulfonyl-amino]-methyl}-phenyl)-acetic acid.
II. 7-{[4-(1-Hydroxy-hexyl)-benzyl]-methanesulfonyl-amino}-heptanoic acid
III. 7-[(4-Hydroxy-nonyl)-methanesulfonyl-amino]-heptanoic acid
IV. 7-[(2'-Hydroxymethyl-biphenyl-4-ylmethyl)-methanesulfonyl-amino]-heptanoic acid
V. 7-[(4-Butyl-benzyl)-methanesulfonyl-amino]-heptanoic acid
VI. 7-{[2-(3,5-Dichloro-phenoxy)-ethyl]-methanesulfonyl-amino}-heptanoic acid
VII. 5-(3-{[3-(3-Chloro-phenyl)-propyl]-methanesulfonyl-amino}-propyl)-thiophene-2-carboxylic acid
VIII. [3-({[3-(3,5-Dichloro-phenyl)-allyl]-methanesulfonyl-amino}-methyl)-phenyl]-acetic acid
IX. N-[2-(3,5-Dichloro-phenoxy)-ethyl]-N-[6-(1H-tetrazol-5-yl)-hexyl]-methanesulfonamide The above listed compounds had more than a 5-fold selectivity for the EP2 receptor subtype in comparison to the EP1, EP3, or EP4 receptor subtypes. The above listed compounds also increased cyclic AMP production, and significantly increased bone formation and bone mineral density in vivo in the above animal models of osteoporosis.

Administration of the compounds of this invention can be via any method which delivers a compound of this invention systemically and/or locally (e.g., at the site of the bone fracture, osteotomy, or orthopedic surgery. These methods include oral routes, parenteral, intraduodenal routes, etc. Generally, the compounds of this invention are administered orally, but parenteral administration (e.g., intravenous, intramuscular, subcutaneous or intramedullary or on sites of bone fracture) may be utilized, for example, where oral administration is inappropriate for the instant target or where the patient is unable to ingest the drug.

The compounds are used for the treatment and promotion of healing of bone fractures and osteotomies by the local application (e.g., to the sites of bone fractures of osteotomies) of the compounds of this invention or compositions thereof. The compounds of this invention are applied to the sites of bone fractures or osteotomies, for example, either by injection of the compound in a suitable solvent (e.g., an oily solvent such as arachis oil) to the cartilage growth plate or, in cases of open surgery, by local application thereto of such compounds in a suitable carrier such as bone-wax, demineralized bone powder, polymeric bone cements, bone sealants etc. Alternatively, local application can be achieved by applying a solution or dispersion of the compound in a suitable carrier onto the surface of, or incorporating it into solid or semi-solid implants conventionally used in orthopedic surgery, such as dacron-mesh, gel-foam and kiel bone, or prostheses.

Two different compounds of this invention can be co-administered simultaneously or sequentially in any order, or a single pharmaceutical composition comprising, for example, a formula I compound as described above and a second compound as described above in a pharmaceutically acceptable carrier can be administered.

In any event the amount and timing of a compound administered will, of course, be dependent on the subject being treated, on the severity of the affliction, on the manner of administration and on the judgement of the prescribing physician. Thus, because of patient to patient variability, the dosages given below are a guideline and the physician may titrate doses of the drug to achieve the treatment (e.g., bone mass augmentation or bone loss prevention) that the physician considers appropriate for the patient. In considering the degree of treatment desired, the physician must balance a variety of factors such as bone mass starting level, age of the patient, presence of preexisting disease, as well as presence of other diseases (e.g., cardiovascular).

In general an amount of a compound of this invention is used that is sufficient to augment bone mass to a level which is above the bone fracture threshold (as detailed in the World Health Organization Study previously cited herein).

In general an effective dosage for the EP2 selective agents described above is in the range of 0.001 to 100 mg/kg/day, preferably 0.01 to 50 mg/kg/day.

The compounds of the present invention are generally administered in the form of a pharmaceutical composition comprising at least one of the compounds of this invention together with a pharmaceutically acceptable vehicle or diluent. Thus, the compounds of this invention can be administered individually or together in any conventional oral, parenteral, rectal or transdermal dosage form.

For oral administration a pharmaceutical composition can take the form of solutions, suspensions, tablets, pills, capsules, powders, and the like. Tablets containing various excipients such as sodium citrate, calcium carbonate and calcium phosphate are employed along with various disintegrants such as starch and preferably potato or tapioca starch and certain complex silicates, together with binding agents such as polyvinylpyrrolidone, sucrose, gelatin and acacia. Additionally, lubricating agents such as magnesium stearate, sodium lauryl sulfate and talc are often very useful for tabletting purposes. Solid compositions of a similar type are also employed as fillers in soft and hard-filled gelatin capsules; preferred materials in this connection also include lactose or milk sugar as well as high molecular weight polyethylene glycols. When aqueous suspensions and/or elixirs are desired for oral administration, the compounds of this invention can be combined with various sweetening agents, flavoring agents, coloring agents, emulsifying agents and/or suspending agents, as well as such diluents as water, ethanol, propylene glycol, glycerin and various like combinations thereof.

For purposes of parenteral administration, solutions in sesame or peanut oil or in aqueous propylene glycol can be employed, as well as sterile aqueous solutions of the corresponding water-soluble salts. Such aqueous solutions may be suitably buffered, if necessary, and the liquid diluent first rendered isotonic with sufficient saline or glucose. These aqueous solutions are especially suitable for intravenous, intramuscular, subcutaneous and intraperitoneal injection purposes. In this connection, the sterile aqueous media employed are all readily obtainable by standard techniques well-known to those skilled in the art.

For purposes of transdermal (e.g., topical) administration, dilute sterile, aqueous or partially aqueous solutions (usually in about 0.1% to 5% concentration), otherwise similar to the above parenteral solutions, are prepared.

Methods of preparing various pharmaceutical compositions with a certain amount of active ingredient are known, or will be apparent in light of this disclosure, to those skilled in this art. For examples of methods of preparing pharmaceutical compositions, see *Remington's Pharmaceutical Sciences*, Mack Publishing Company, Easter, Pa., 15th Edition (1975).

Pharmaceutical compositions according to the invention may contain 0.1%–95% of the compound(s) of this invention, preferably 1%–70%. In any event, the composition or formulation to be administered will contain a quantity of a compound(s) according to the invention in an amount effective to treat the disease/condition of the subject being treated, e.g., a bone disorder.

The compounds of this invention either alone or in combination with each other or other compounds generally will be administered in a convenient formulation. The following formulation examples only are illustrative and are not intended to limit the scope of the present invention.

In the formulations which follow, "active ingredient" means a compound of this invention.

Formulation 1: Gelatin Capsules
Hard gelatin capsules are prepared using the following:

| Ingredient | Quantity (mg/capsule) |
| --- | --- |
| Active ingredient | 0.25–100 |
| Starch, NF | 0–650 |
| Starch flowable powder | 0–50 |
| Silicone fluid 350 centistokes | 0–15 |

A tablet formulation is prepared using the ingredients below:

Formulation 2: Tablets

| Ingredient | Quantity (mg/tablet) |
| --- | --- |
| Active ingredient | 0.25–100 |
| Cellulose, microcrystalline | 200–650 |
| Silicon dioxide, fumed | 10–650 |
| Stearate acid | 5–15 |

The components are blended and compressed to form tablets.

Alternatively, tablets each containing 0.25–100 mg of active ingredients are made up as follows:

Formulation 3: Tablets

| Ingredient | Quantity (mg/tablet) |
| --- | --- |
| Active ingredient | 0.25–100 |
| Starch | 45 |
| Cellulose, microcrystalline | 35 |
| Polyvinylpyrrolidone (as 10% solution in water) | 4 |
| Sodium carboxymethyl cellulose | 4.5 |
| Magnesium stearate | 0.5 |
| Talc | 1 |

The active ingredients, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

Suspensions each containing 0.25–100 mg of active ingredient per 5 ml dose are made as follows:

Formulation 4: Suspensions

| Ingredient | Quantity (mg/5 ml) |
| --- | --- |
| Active ingredient | 0.25–100 mg |
| Sodium carboxymethyl cellulose | 50 mg |
| Syrup | 1.25 mg |
| Benzoic acid solution | 0.10 mL |
| Flavor | q.v. |
| Color | q.v. |
| Purified Water to | 5 mL |

The active ingredient are passed through a No. 45 mesh U.S. sieve and mixed with the sodium carboxymethyl cellulose and syrup to form smooth paste. The benzoic acid solution, flavor, and color are diluted with some of the water and added, with stirring. Sufficient water is then added to produce the required volume. An aerosol solution is prepared containing the following ingredients:

Formulation 5: Aerosol

| Ingredient | Quantity (% by weight) |
| --- | --- |
| Active ingredient | 0.25 |
| Ethanol | 25.75 |
| Propellant 22 (Chlorodifluoromethane) | 70.00 |

The active ingredient is mixed with ethanol and the mixture added to a portion of the propellant 22, cooled to 30° C., and transferred to a filling device. The required amount is then fed to a stainless steel container and diluted with the remaining propellant. The valve units are then fitted to the container. Suppositories are prepared as follows:

Formulation 6: Suppositories

| Ingredient | Quantity (mg/suppository) |
| --- | --- |
| Active ingredient | 250 |
| Saturated fatty acid glycerides | 2,000 |

The active ingredient is passed through a No. 60 mesh U.S. sieve and suspended in the saturated fatty acid glycerides previously melted using the minimal necessary heat. The mixture is then poured into a suppository mold of nominal 2 g capacity and allowed to cool.

An intravenous formulation is prepared as follows:

Formulation 7: Intravenous Solution

| Ingredient | Quantity |
| --- | --- |
| Active ingredient | 20 mg |
| Isotonic saline | 1,000 mL |

The solution of the above ingredients is intravenously administered to a patient at a rate of about 1 mL per minute.

The active ingredient above may also be a combination of agents.

It should be understood that the invention is not limited to the particular embodiments described herein, but that various changes and modifications may be made without departing from the spirit and scope of this novel concept as defined by the following claims.

What is claimed is:

1. A method for stimulating bone formation and increasing bone mass in a mammal comprising selectively agonizing an EP2 receptor subtype by administering to a mammal a therapeutically effective amount of a selective EP2 receptor subtype agonist.

2. A method for treating a mammal which presents with low bone mass comprising selectively agonizing an EP2 receptor subtype by administering to said mammal a therapeutically effective amount of a selective EP2 receptor subtype agonist.

3. The method as recited in claim 2 wherein osteoporosis, osteotomy, childhood idiopathic bone loss or bone loss associated with periodontitis is treated.

4. The method as recited in claim 3 wherein osteoporosis is treated.

5. The method as recited in claim 2 wherein the mammal is a human.

6. The method as recited in claim 5 wherein the human is a man or a post-menopausal woman over the age of 60.

7. The method as recited in claim 2 wherein the EP2 agonist is at least 10 fold selective for the EP2 receptor subtype over the EP1, EP3 and EP4 receptor subtypes.

8. The method as recited in claim 7 wherein the EP2 agonist is at least 100 fold selective for the EP2 receptor subtype over the EP1, EP3 and EP4 receptor subtypes.

9. The method as recited in claim 2 wherein about 0.001 to 100 mg/kg/day of the selective EP2 agonist is administered.

10. The method as recited in claim 2 wherein about 0.01 to 50 mg/kg/day of the EP2 agonist is administered.

11. The method as recited in claim 2 wherein secondary osteoporosis is treated.

12. The method as recited in claim 11 wherein glucocorticoid-induced osteoporosis, hyperthyroidism-induced osteoporosis, immobilization-induced osteoporosis, heparin-induced osteoporosis or immunosuppressive-induced osteoporosis is treated.

13. A method for treating a bone fracture in a mammal by selectively agonizing an EP2 receptor subtype by administering to a mammal suffering from a bone fracture a therapeutically effective amount of a selective EP2 receptor subtype agonist.

14. The method as recited in claim 13 wherein EP2 selective agonist is applied locally to the site of bone fracture.

15. The method as recited in claim 13 wherein the mammal is a human.

16. The method as recited in claim 13 wherein the EP2 agonist is at least 10 fold selective for the EP2 receptor subtype over the EP1, EP3 and EP4 receptor subtypes.

17. The method as recited in claim 13 wherein the EP2 agonist is at least 100 fold selective for the EP2 receptor subtype over the EP1, EP3 and EP4 receptor subtypes.

18. The method as recited in claim 13 wherein about 0.01 to 10 mg/kg/day of the EP2 agonist is administered.

19. A method for enhancing bone healing following facial reconstruction, maxillary reconstruction or mandibular reconstruction, enhancing long bone extension, enhancing the healing rate of a bone graft, enhancing prosthetic ingrowth, or inducing vertebral synostosis in a mammal by selectively agonizing the EP2 receptor subtype by administering to a mammal a therapeutically effective amount of a selective EP2 receptor subtype agonist.

* * * * *